United States Patent
Estabrook et al.

(10) Patent No.: US 6,506,182 B2
(45) Date of Patent: *Jan. 14, 2003

(54) METHOD FOR SUBCUTANEOUS ACCESS TO THE VASCULAR SYSTEM OF A PATIENT

(75) Inventors: Brian K. Estabrook, Foxboro, MA (US); Paul J. Smith, Smithfield, RI (US)

(73) Assignee: Biolink Corporation, Mansfield, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/226,956

(22) Filed: Jan. 8, 1999

(65) Prior Publication Data

US 2001/0049503 A1 Dec. 6, 2001

Related U.S. Application Data

(63) Continuation-in-part of application No. 08/661,903, filed on Jun. 12, 1996, now Pat. No. 6,013,058.

(51) Int. Cl.[7] .............................................. A61M 5/178
(52) U.S. Cl. ................... 604/164.11; 604/174; 604/905
(58) Field of Search .......................... 604/93, 167, 169, 604/174, 175, 246, 247, 256, 264, 891.1, 164.01, 164.02, 164.04, 164.09, 164.12, 170.01, 170.02, 93.01, 167.01, 167.06, 523, 905, 533–535; 128/DIG. 26, 912; 251/149.1

(56) References Cited

U.S. PATENT DOCUMENTS

| | | | |
|---|---|---|---|
| 4,808,156 A | | 2/1989 | Dean |
| 5,098,410 A | * | 3/1992 | Kerby et al. ................. 604/256 |
| 5,207,648 A | | 5/1993 | Gross |
| 5,281,199 A | * | 1/1994 | Ensminger et al. ........... 604/93 |
| 5,382,239 A | * | 1/1995 | Orr et al. ..................... 604/177 |
| 5,549,554 A | | 8/1996 | Miraki |
| 3,467,096 A | | 9/1996 | Horn |
| 5,637,074 A | * | 6/1997 | Andino et al. ................ 600/29 |
| 5,771,914 A | | 6/1998 | Ling et al. |
| 5,911,706 A | | 6/1999 | Estabrook et al. |

* cited by examiner

*Primary Examiner*—Brian L. Casler
*Assistant Examiner*—LoAn H. Thanh
(74) *Attorney, Agent, or Firm*—Pandiscio & Pandiscio

(57) ABSTRACT

A needle and obturator assembly for access to entrance lumens in an access device disposed subcutaneously in a body of a mammal, for transfer of fluid into and/or out of the mammal body, comprising a first needle and obturator unit for insertion through a skin portion of the mammal body and into a first of the lumens of the access device, a second needle and obturator unit for insertion through the skin portion of the mammal body and into a second of the lumens of the access device, and hub structure for supporting the first and second needle and obturator units in fixed, spaced-apart positions relative to each other after complete insertion of the first and second needle and obturator units in the respective lumens. The first and second obturators are withdrawable from their respective needles to open first and second passageways in the respective needles for the transfer of fluid into and/or out of the access device.

9 Claims, 15 Drawing Sheets

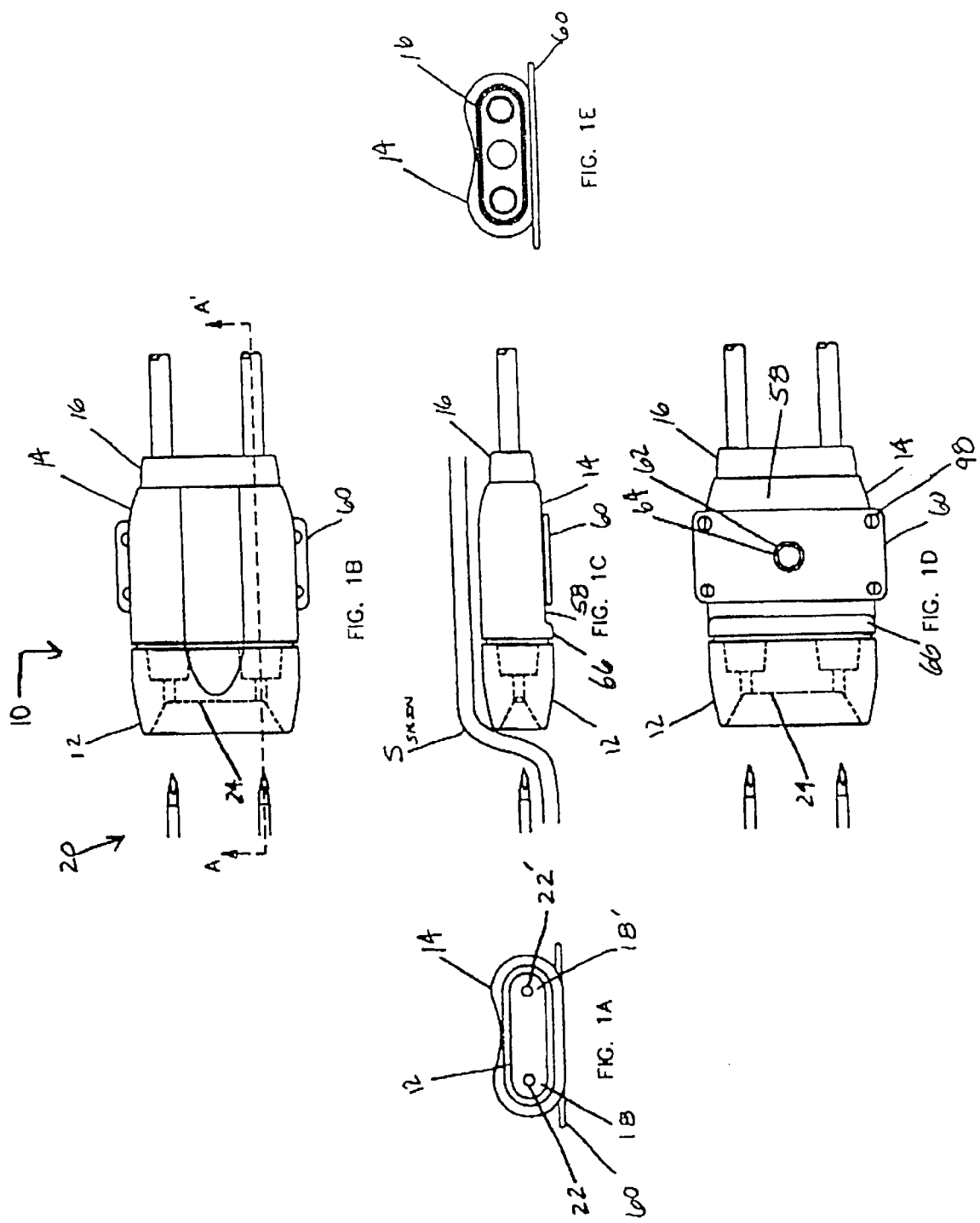

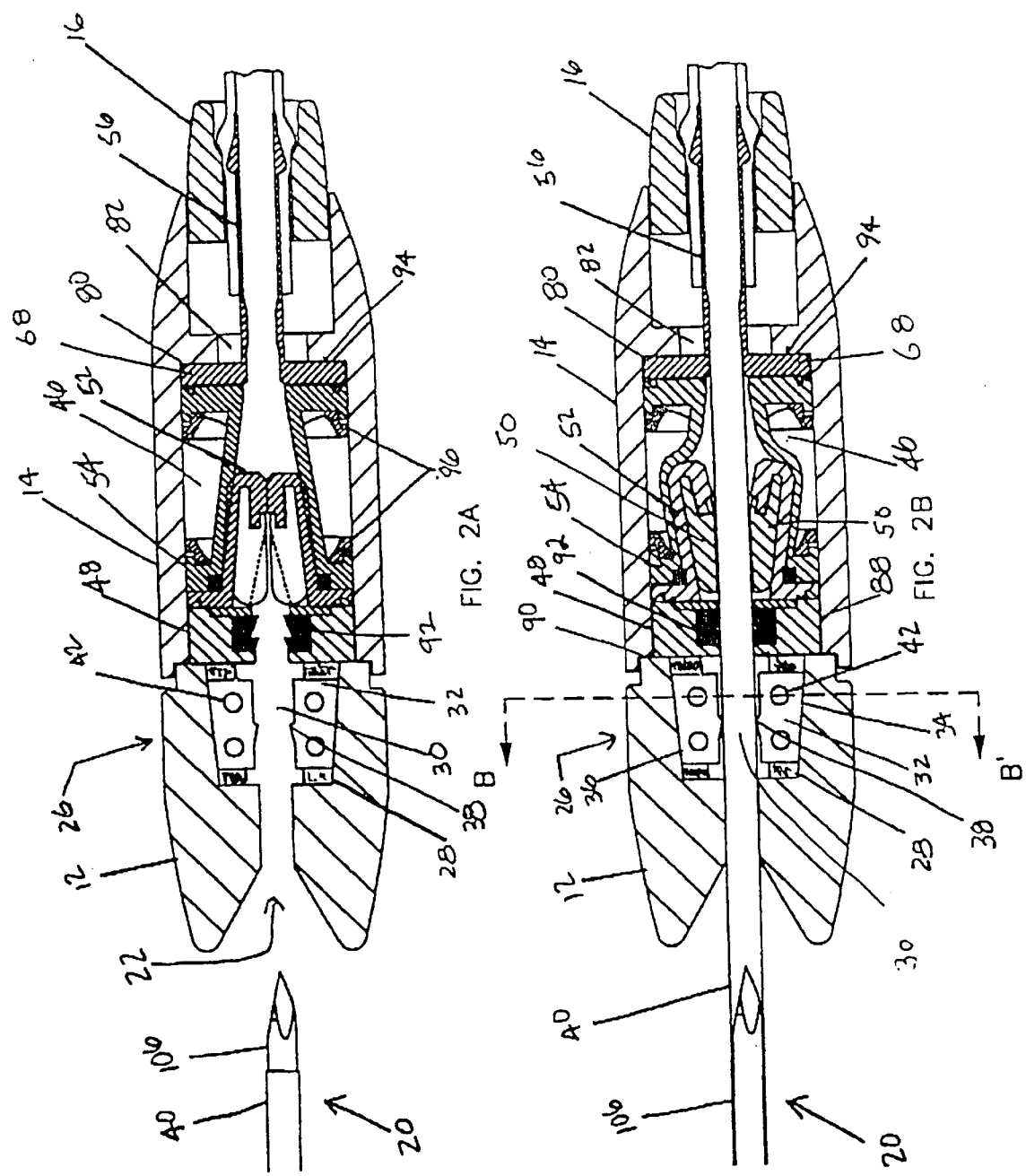

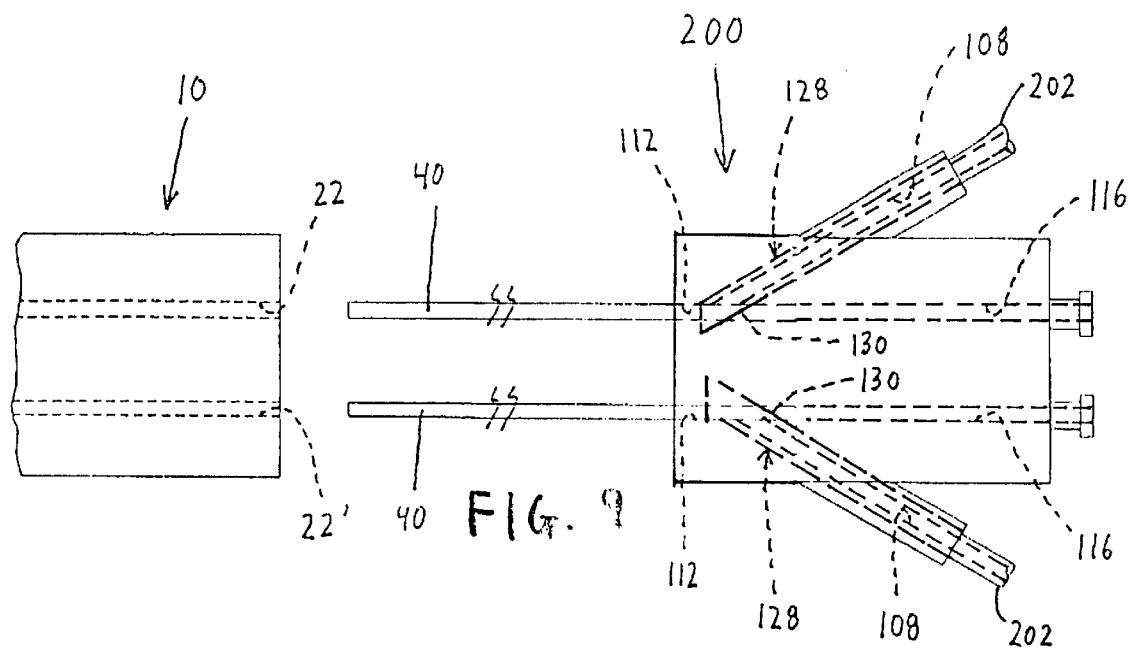
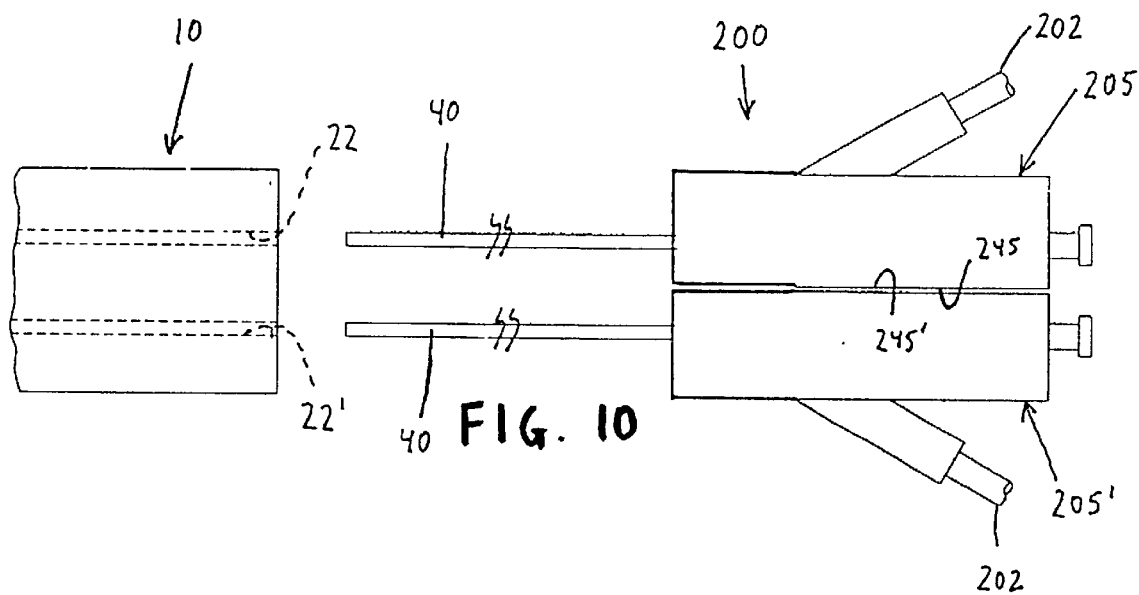

METHOD FOR SUBCUTANEOUS ACCESS TO THE VASCULAR SYSTEM OF A PATIENT

CROSS-REFERENCE TO RELATED PATENT APPLICATIONS

This is a continuation-in-part of pending prior U.S. patent application Ser. No. 08/661,903, filed Jun. 12, 1996 by Brian K. Estabrook et al. for DEVICE FOR SUBCUTANEOUS ACCESSIBILITY.

FIELD OF THE INVENTION

The present invention relates generally to apparatus that allows access to the vascular system of a human (or other animal), particularly for the high-volume fluid flow required in hemodialysis, plasmapheresis and other fluid exchange therapies. More particularly, the present invention relates to a septum-less, subcutaneously-implantable access device of single or dual-lumen construct, and mating needle apparatus.

BACKGROUND OF THE INVENTION

There exists a class of devices for accessing fluid spaces and vessels within a human (or animal) body that are generally referred to as "ports". Herein, "vessel" is defined as any conduit carrying a fluid within the patient's body. These prior art port devices generally comprise a chamber having an access opening sealed by means of a septum and having an egress from a second location leading to a catheter which is disposed within a fluid space or vessel. The septum allows a hollow needle (or "cannula") to pass into the port's chamber, but then closes when the needle is removed, thereby preventing fluid leakage from within the bodily fluid space or vessel and also preventing anything from entering or exiting the port's chamber. These port devices are usually implantable below the skin so as to prevent infection, other contamination and mishandling.

Prior art ports are designed for relatively infrequent use, perhaps once a week, and, importantly, for fluid flow rates of 50 milliliters per minute or less, as is common during chemotherapeutic treatment. Modification of these prior art port devices for hemodialysis, plasmapheresis and other fluid exchange therapies, which require much greater flow rates, by simply enlarging the device components, poses several serious drawbacks that effectively limit use in such high-volume applications.

First, the prior art port's septum degrades quickly due to the larger gauge needles necessary to accommodate the higher flow rates required in hemodialysis. Repeated puncturing of the septum by these large needles produces numerous free-floating septum fragments that can find their way into the patient's circulatory system. Accordingly, the useful life of the port device is substantially shortened, thereby defeating one of the purposes of using an implantable subcutaneous access device.

Second, the prior art port's flow path has several stagnation points where clots may form, and the port is also not completely flushable or easily cleaned, thereby providing breeding grounds for infection, once contaminated, or a build-up of material which may adversely affect function.

Third, the prior art port's flow path is not streamlined and contains flow path obstructions, sharp corners, and abrupt changes in flow area and flow direction. This tends to increase the shear stress and turbulences experienced by blood flowing through the port device due to the significantly higher flow rates required in hemodialysis, thereby increasing erythrocyte damage and platelet activation. Also, the prior art port's tortuous flow path increases the flow path resistance and the pressure drop through the port device; such effects can increase air release and foaming, thereby causing the dialysis machine's safety alarms to activate.

A general limitation in all relevant prior art port devices is the lack of a streamlined flow path. Without such streamlining, stagnant volumes exist where clots may form and shear stress is higher, tending towards erythrocytic damage. Such locations cannot be flushed or easily cleaned. Blood residue remaining in the devices after flushing may clot and may provide breeding grounds for infection, once contaminated. In addition, pressure drops and abrupt flow direction changes may damage blood components.

The present invention is also useful for other liquid or fluid (including gases) transfer purposes into and out of human and animal bodies, including the transfer of externally-prepared solutions for cleaning, flushing, dialysis, chemical agent delivery, transfusions, blood donation, insufflation, wound drainage, etc.

Accordingly, it is a principal object of this invention to overcome the above-illustrated inadequacies and problems of extant devices by providing a totally implantable access means suitable for repeated use in applications (e.g., hemodialysis) with blood flow rates of 250 milliliters per minute or more, yet with low pressure drops along the flow path.

It is another principal object of the present invention to optimize fluid flow, in hemodialysis particularly, and in other applications referred to generally, above.

It is another object of this invention to provide a substantially laminar flowstream.

It is yet another object of this invention to minimize flow discontinuities and to substantially match the internal diameters of the injecting needle (or cannula) and the receiving catheter, and a related object is to bring the exit end of the needle (or cannula) and the entrance end of the catheter into close proximity.

It is a further object of this invention to provide access means where the flow path is streamlined and provides substantially no stagnation points and no flow discontinuities, and also to provide an apparatus where the entire flowstream is flushable.

It is a further object of the present invention to minimize internal fluid collection zones or stagnant volumes in such an access device.

It is a still further object of this invention to have lower clotting, stenosis and infection rates than with synthetic grafts.

It is yet another object of this invention to have lower infection and lumen clotting rates than with percutaneous catheters.

It is a still further object of this invention to provide apparatus suitable for single and dual-lumen catheter systems.

It is yet another object of this invention to provide an access device that is less painful during needle (or cannula) insertion and more accommodating during dialysis for the patient.

It is a further object of the present invention to minimize irritation and other adverse effects associated with intermittent skin punctures over a course of days, months or years of repetitive subcutaneous access.

It is a further object of this invention to secure the needle (or cannula) within the access device during the dialysis session.

It is a further object of the present invention to enhance the access device so as to more effectively lock in a needle (or cannula) to the access device in order to avoid inadvertent separation, yet allow ease of deliberate release of the needle (or cannula).

It is a further object of the present invention to provide ease of manufacture and assembly of such an access device consistent with enhanced locking.

A further object of the present invention is to establish economy of the lock devices for disposability.

It is a further object of the present invention to provide enhanced needle (or cannula) and obturator handling external to a patient via hub devices coordinated with the structure and functions of the locking devices.

It is another object of the present invention, when using dual-lumen catheters, to secure both needles (or cannulas) to each other.

And another object of the present invention is to provide improved needle (or cannula) and obturator assemblies.

It is also an object of the present invention to accommodate multiples of the foregoing objects together.

SUMMARY OF THE INVENTION

The foregoing objects are met by a single subcutaneously-implantable device for accessing a vessel within a patient's body, or a ganged pair of such devices or separate such devices, each device including (a) access guidance means having an entrance and a passageway for receiving a needle (or cannula) and accommodating a locking means for the needle (or cannula), (b) flexible locking means, (c) needle guidance means of sufficient hardness to prevent scoring or chipping, (d) valve means for allowing access to a vessel when a needle (or cannula) is inserted into the device and preventing fluid flow through the device when the needle (or cannula) is withdrawn from the device, the valve means having a closable passageway that accepts an inserted needle (or cannula) and comprising an access portion, a sealing portion, and a distal portion; (e) a catheter attachment having a closable passageway with seating means disposed therein, and (f) a shell capable of enclosing these elements.

A resilient elastomeric means for producing a contact sealing pressure is arranged around the sealing portion of the valve means. This resilient elastomeric means includes, in a preferred embodiment, a cylindrical band made of an elastomeric material that provides forces on the sealing portion and is located outside the fluid path. The sealing portion ordinarily prohibits fluids from passing through the seal. But when a mechanical device (e.g., a needle or cannula assembly) is inserted percutaneously, and guided to the valve's access portion by the access guidance means, the mechanical device (e.g., the needle or cannula assembly) engages the needle guidance means disposed within the access portion of the valve with sufficient axial force to overcome the radial force exerted on the sealing portion by the resilient means for sealing. It is important to note that the needle (or cannula) assembly forces the guidance means, and the guidance means pushes the sealing portion open. The needle (or cannula) assembly, actually an obturator which is part of the needle (or cannula) assembly in a preferred embodiment, then enters the opened sealing means without the point of the obturator puncturing or cutting the sealing means. The needle guidance means itself opens a slit to allow the needle (or cannula) assembly to enter and then to slip through the sealing means. So in this fashion the needle (or cannula) assembly passes through the valve until the needle (or cannula) assembly engages the catheter attachment seating means. This operation provides access through the valve to the valve's distal portion and, ultimately, to the vessel lumen, as the distal portion of the catheter (that is attached to the access device via the catheter attachment) extends into a vessel lumen.

An advantage of the present invention is found by minimizing the spacing between the end of the needle (or cannula) and the beginning of the catheter, and by smoothly fairing the internal surfaces of the short connecting or transition passageway to the interior surfaces of the needle (or cannula) and the catheter. If there are disparate internal diameters, the short connecting transition passageway smoothly and uniformly accommodates the internal diameters. This arrangement provides a flow path with minimum flow discontinuities and a path that is easily flushed.

The catheter may be flexibly attached to the surrounding tissue supporting the catheter, but the flexibility allows the access device's position to move relative to the surrounding tissue. A strain relief assembly may also be provided at the catheter attaching end of the access device so as to relieve tension on the catheter attachment to the access device, whereby to prevent catheter kinking. Edges of the strain relief structure can be sutured or stapled to adjacent tissue, and the strain relief wrap can in turn hold other portions of the access device.

The access device may be flexibly anchored to the surrounding tissue. In a preferred embodiment, such anchor means are attached to the access device so as to allow the needle (or cannula) entrance of the access device to be rotated, preferably by as much as 50 degrees relative to the anchor means in at least two directions. This, together with the normal movement of the skin, allows the needle (or cannula) assembly to enter the skin at a location on the skin that is healed, or at least a skin location that has had ample time to heal. This ability to access larger areas of skin for inserting the needle (or cannula) assembly is a significant advantage over relatively fixed ports.

The resilient means for sealing is arranged and constructed so as to close the valve's potential lumen such that the longitudinal transition profile of the valve's access portion forms a particular shape. The shape of the access portion allows for the generally conical point of the needle (or cannula) assembly's obturator to open or push apart the access portion, and the slit in the sealing portion, with a wedging action as the obturator's point is pushed through the seal. The axial point-pushing force overcomes the radial biasing force exerted by the resilient means for sealing, and the internal stresses of the sealing portion, as the obturator's point enters the sealing portion, without cutting the valve material. Because no cutting occurs, no particles of valve material are generated, as is common with septums in ports now in use. Furthermore, the number of penetration cycles to failure in the present invention is significantly higher than with septum ports, as negligible damage occurs during needle (or cannula) penetration.

The flow path transitions between the needle (or cannula) lumen, the short connecting passage in the access device, and the catheter lumen are arranged and constructed so as to provide for maximum smoothness and continuous flow paths without abrupt changes in flow diameter and only gentle changes in flow direction. All narrowing and broadening of the flow path is gradual, with angles of preferably 25 degrees or less.

The invention also provides for a hollow needle (or cannula) apparatus with an outside diameter that matingly corresponds to the entry passageway of the access device, and an obturator that is inserted into the needle (or cannula) lumen, filling the lumen, and which has a tip portion that extends beyond the needle (or cannula). This needle/obturator combination provides a needle (or cannula) assembly with a pointed end, and an outer surface having smooth transitions, which are formed to puncture tissue easily and to open the valve without damaging it. The hollow needle (or cannula) is preferably made of metal so that the needle wall may be formed as thin as possible considering the stresses on the needle. This is important, since the larger the internal diameter of the needle (or cannula), the lower is the flow resistance. The lowest flow resistance consistent with the physical constraints and needs of the patient and the function being performed, especially in the high flow rate hemodialysis field, is an important goal of the present invention and a major advantage of the present invention.

The flexible lock preferably comprises a resilient plug (preferably made of a medical quality elastomer) surrounding an inserted hollow metal needle (or cannula), but containing rigid internal blades or strips (preferably made of a super hard material such as a hard ceramic or hardened metal, e.g. titanium nitride) that extend radially in locking use and are configured and arranged to inscribe the outer needle (or cannula) surface and bear on it with a high reaction force. When an inadvertent axial pull on the needle (or cannula) from outside, or the push of a muscular contraction from within, places an expelling force on the needle (or cannula), the beginning of movement increases the locking effect. The blades or strips have inner edges that form one or more teeth of pointed or blunt ends, such teeth having shallow clearance angles with respect to the passage axis. The blades have outer edges that are locked in geometrically by a tapered inner surface of the shell. Deliberate removal can be done by rotating and/or wiggling (spiral or a combination of axial/rotational movements) of the needle (or cannula) so that the orientation of the blades shifts, from essentially radial to essentially chordal or non-radial alignment relative to the access device's internal passage axis. When the plug and blades are disposed non-radially, the needle (or cannula) can be withdrawn easily. The rotation or the like is then relaxed (after complete removal of the needle or cannula) and the blades are restored to radial alignment by the elasticity of the plug. When the needle (or cannula) is thereafter re-inserted into the access device, typically one or more days later, the entering needle (or cannula) passes through the inner edges of the blades.

Generally there is a full withdrawal of a needle (or cannula) or a full insertion; but partial insertion and/or partial withdrawal can also be accommodated. The resilient plug body is set radially apart from the needle (or cannula) surface so as to avoid shedding or uneven friction due to thermal conditions or other sources of expansion/contraction of the flexible plug (e.g., made of silicone rubber). The flexible plug material is preferably cast in a mold about the aligned (radial) blades. Holes or the equivalent are preferably provided in the blades so that the flexible material on both sides of each blade is bridged via such holes or other means, and the blades are securely aligned therein, radially and with inner and outer edges of the blades extending beyond inner and outer plug surfaces. Generally, there is a low-axial-direction friction meeting of the blade outer edges and the tapered (frusto-conical) shell inner surface. A ceramic shell with a smooth-finish, inner-tapered surface meets this criterion very well. Similarly, the blade inner edges slide along the needle (or cannula) outer surface with low friction. The hardness of all such surfaces, and the rigidity and dimensional stability of blades, needle (or cannula) and shell, are related to the above features and also important per se.

The valve, in a preferred embodiment, may include a plug of sealing material with a slit cut in the center, and with a spring loading means holding the slit closed, so as to block the internal passage of the access device when the needle (or cannula) is withdrawn and yet is readily opened as the leading portion of the needle (or cannula) assembly (i.e., the obturator) is inserted, without damage, as described above. Similar valves can be used with more than one slit opening and closing as described above. In any such design, it is preferable to have automatic, spring-loaded closing when the needle (or cannula) is withdrawn, and easy opening as a needle (or cannula) assembly, or the like, is inserted through the access device's internal passage, so as to maintain contact sealing stress when the valve is closed. The present invention causes no cutting due to the manner of opening the seal described above.

Ease of use and product reliability are also accommodated by the features discussed above and below.

The invention also includes an extracorporeal needle (or cannula) assembly hub structure, or pair of such structures, usable in combination with the implantable subcutaneous access device(s) for straight needle (or cannula) alignment, and an aligned cutter and stiffener (a separate element or integrated with the needle or cannula) that has to penetrate the skin, find the entrance to the inner passage of the subcutaneous access device and pass through it to a lock-in site therein without coring the skin. The hub structure preferably has a Y-connection of three internal paths: (a) external fluid passage, (b) passage to the needle or cannula, and (c) a cannula/cutter access leg, all cooperating with shallow bend angles and gradual curvatures at the Y-intersection in the fluid path, and straight line access to the needle (or cannula) assembly locking device, as consistent with practical and economic mass production, while achieving a benign flow path which does not damage cellular blood components and meets previously stated criteria for the blood path.

The needle (or cannula) is initially inserted through the hub structure (or comes pre-assembled with it) and has an internal obturator with a point that passes out of the needle (or cannula) distal end for penetrating skin and subcutaneous tissue and serving as an aid to finding the subcutaneous entrance to the access and lock device. The obturator point is faceted so that its cutting is done along meeting-line edges of the facets. However, when the obturator point has cutting edges that extend from the center towards the outer surface of the obturator, as the cutting edges extend to the outer surface of the obturator, the edges are preferably softened or dulled so that the obturator does not cut, score or otherwise mar the internal wall of the passage or the interiors of the locking and sealing components of the access device which form part of the passage. The obturator edges are softened in a preferred embodiment by facets, but in a larger number of facets, set at shallower angles, than the facets at the obturator's point. In yet another preferred embodiment, the facets are concave rather than flat, where the intersection of the facets provides a sharper edge. The section of the obturator with the dulled edges blends into a beveled end of the needle (or cannula).

Once the needle (or cannula) assembly is fully inserted in the access device, and locked and sealed in place, the obturator can be withdrawn from the needle (or cannula) so as to leave a smooth flow path beginning in the needle (or cannula) hub structure and continuing therein to a smooth blending with the proximal needle (or cannula) region of the hub structure, and continuing through the full length of the needle (or cannula) to emerge at the distal end and, in turn, blend smoothly with the access device's internal transition passage, and then into the implantable catheter within the patient.

The access device of the present invention is suitable for both single-needle and standard (i.e., dual-needle) hemodialysis, plasmapheresis and fluid exchange therapy applications. For standard applications, which require two flow paths, the access device's housing may be arranged and constructed to engage two needle (or cannula) hub assemblies, as described above, and include dual-lumen through-passageways. When two needles and needle hubs are used, a bar may be provided that engages each needle hub, thereby locking both needles to each other to preclude inadvertent disconnection of only one needle, thereby enhancing patient safety. In another preferred embodiment, the two needle hubs are prevented from moving laterally with respect to each other.

It is important to note that a primary object of this invention is to provide an implantable, subcutaneous access device suitable for applications requiring flow rates of 250 milliliters per minute or greater, with low pressure drops along a streamlined flow path having substantially no stagnation points or other flow discontinuities. Low pressure drops and substantial elimination of stagnation points are achieved by having maximum internal diameters of the flow path (and, therefore, thinnest needle or cannula walls), smooth transition points where different elements of the access device abut (e.g., the cannula-transition element-catheter interface) and by having all changes in lumen diameter be of a gradual nature and having a straight, or nearly straight, flow path without sharp curves or objects protruding into the flow path, and no dead volume.

As indicated above, because such large flow rates are desired with low resistance, it is preferable to have the largest needle (or cannula) outside diameter that patients will accept. Accordingly, rigidity of the puncture needle (or cannula) is desired. A rigid needle (or cannula) allows a greater inner lumen diameter per outer component diameter (i.e., thinner walls) than does a flexible tube. This is important, because it allows the needle (or cannula) to have as small a cross-sectional diameter as possible, thereby lessening the trauma on the patient's puncture site, yet still being capable of handling large flow rates. Flexible tubes require much higher outer diameter-to-inner diameter aspect ratios in order to prevent kinking or tube collapse. Thus, to accommodate the substantial bloodflows common during hemodialysis, a much larger outer diameter needle (or cannula) would be required if flexible materials were used. Also, a rigid needle (or cannula) allows a greater force to be transmitted to open the seal valve by overcoming the resistance provided by the biasing means. Thus, a greater contact sealing force can be employed where the needle (or cannula) is rigid, resulting in a more robust, reliable, and fault-tolerant valve seal.

Further, the lack of sharp angles or bends in the flow path is much less injurious to fragile hematocytes. Since the flow path from needle (or cannula) to catheter, or vice versa, is substantially straight, the fluid turbulence is minimized, the shear stresses are lessened, and the flow directional changes are minimized, resulting in less erythrocyte damage and a lowered tendency toward platelet activation.

A medically-acceptable, water-based lubricant can also be used on the needle (or cannula) exterior, as an enhanced lifespan has been observed when such a lubricant is used. Also, a lubricated needle (or cannula) will generally penetrate the skin with less pain to the patient.

The invention further provides a needle (or cannula) and obturator assembly for access to entrance lumens in an access device disposed subcutaneously in a body of a mammal, for transfer of fluid into and/or out of the mammal body. The needle (or cannula) and obturator assembly comprises a first needle (or cannula) and obturator unit for insertion through a skin portion of the mammal body and into a first of the lumens of the access device, a second needle (or cannula) and obturator unit for insertion through the skin portion of the mammal body and into a second of the lumens of the access device, and hub structure for supporting the first and second needle (or cannula) and obturator units in fixed, spaced-apart positions relative to each other after complete insertion of the first and second needle (or cannula) and obturator units in the respective lumens. The first and second obturators are withdrawable from their respective needles (or cannulas) to open first and second passageways in the respective needles (or cannulas) for the transfer of fluid into and/or out of the access device.

The invention further provides a method for accessing an access device disposed subcutaneously in a body of a mammal and having entrance lumens for transfer of fluid into and out of the mammal body, the method comprising the steps (1) providing a needle (or cannula) and obturator assembly, the needle (or cannula) and obturator assembly comprising a first needle (or cannula) and obturator unit for insertion through a skin portion of the mammal body and into a first of the lumens of the access device, a second needle (or cannula) and obturator unit for insertion through the skin portion of the mammal body and into a second of the lumens of the access device, and hub structure for supporting the first and second needle (or cannula) and obturator units, the hub structure comprising a hub body having the first and second needle (or cannula) and obturator units fixed therein, (2) advancing the first and second needle (or cannula) and obturator units substantially simultaneously through the skin portion and into the first and second lumens, respectively, and (3) withdrawing obturator portions of the first and second needle (or cannula) and obturator units to provide passageways between the access device and the hub body for flow of fluid therebetween.

The invention still further provides a method for accessing an access device disposed subcutaneously in a body of a mammal and having entrance lumens for transfer of fluid into and out of the mammal body, the method comprising the steps of (1) providing a needle (or cannula) and obturator assembly, the needle (or cannula) and obturator assembly comprising a first needle (or cannula) and obturator unit for insertion through a skin portion of the mammal body and into a first of the lumens of the access device, a second needle (or cannula) and obturator unit for insertion through the skin portion of the mammal body and into a second of the lumens of the access device, and hub structure for supporting the first and second needle (or cannula) and obturator units, the hub structure comprising first and second hub bodies having the first and second needle (or cannula) and obturator units, respectively, fixed therein, (2) connecting the first needle (or cannula) and obturator unit to the second needle (or cannula) and obturator unit, (3) advancing the first and second needle (or cannula) and obturator units substantially simultaneously through the skin portion and into the first and second lumens, respectively, and (4) withdrawing needle portions of the first and second needle (or cannula) and obturator units to provide passageways between the access device and the hub bodies for flow of fluid therebetween.

The invention still further provides a method for accessing an access device disposed subcutaneously in a body of a mammal and having entrance lumens for transfer of fluid into and out of the mammal body, the method comprising the steps of (1) providing a needle (or cannula) and obturator assembly, the needle (or cannula) and obturator assembly comprising a first needle (or cannula) and obturator unit for insertion through a skin portion of the mammal body and into a first of the lumens of the access device, a second needle (or cannula) and obturator unit for insertion through the skin portion of the mammal body and into a second of the lumens of the access device, and hub structure for supporting the first and second needle (or cannula) and obturator units, the hub structure comprising first and second hub bodies having the first and second needle (or cannula) and obturator units, respectively, fixed therein, (2) advancing the first and second needle (or cannula) and obturator units individually through the skin portion and into the first and second lumens, respectively, (3) connecting the first needle (or cannula) and obturator unit to the second needle (or cannula) and obturator unit, and (4) withdrawing needle portions of the first and second needle (or cannula) and obturator units to provide passageways between the access device and the hub bodies for flow of fluid therebetween.

The invention still further provides a needle assembly comprising a needle having a distal end and a proximal end, the needle comprising a first lumen; a distal body element having a distal end and a proximal end, the distal end of the distal body element being mounted to the proximal end of the needle, and the distal body element comprising a second lumen, with the second lumen being in communication with the first lumen; a compressible tube having a distal end and a proximal end, the distal end of the compressible tube being mounted to the proximal end of the distal body element, and the compressible tube comprising a third lumen, with the third lumen being in communication with the second lumen; a proximal body element having a distal end and a proximal end, the distal end of the proximal body element being mounted to the proximal end of the compressible tube, and the proximal body element comprising a fourth lumen, with the fourth lumen being in communication with the third lumen; closure means connected to the compressible tube for selectively closing off the third lumen; and a cap having a distal end and a proximal end, the distal end of the cap being removably mounted to the proximal end of the proximal body element, and the cap comprising a fifth lumen, the fifth lumen being in communication with the fourth lumen when the cap is mounted to the proximal body element, and the cap comprising a septum extending transversely across the fifth lumen.

The invention still further provides a method for accessing the vascular system of a patient, the method comprising the steps of (1) providing a needle and obturator assembly comprising a needle having a distal end and a proximal end, the needle comprising a first lumen; a distal body element having a distal end and a proximal end, the distal end of the distal body element being mounted to the proximal end of the needle, and the distal body element comprising a second lumen, with the second lumen being in communication with the first lumen; a compressible tube having a distal end and a proximal end, the distal end of the compressible tube being mounted to the proximal end of the distal body element, and the compressible tube comprising a third lumen, with the third lumen being in communication with the second lumen; a proximal body element having a distal end and a proximal end, the distal end of the proximal body element being mounted to the proximal end of the compressible tube, and the proximal body element comprising a fourth lumen, with the fourth lumen being in communication with the third lumen; closure means connected to the compressible tube for selectively closing off the third lumen; a cap having a distal end and a proximal end, the distal end of the cap being removably mounted to the proximal end of the proximal body element, and the cap comprising a fifth lumen, the fifth lumen being in communication with the fourth lumen when the cap is mounted to the proximal body element, and the cap comprising a septum extending transversely across the fifth lumen; an obturator having a distal end and a proximal end, the obturator being removably disposed in the first lumen, the second lumen, the third lumen, the fourth lumen and the fifth lumen, with the obturator passing through the septum when the obturator is disposed in the fifth lumen; and locking means connected to the proximal end of the obturator for selectively locking the obturator to the cap; (2) passing the needle assembly through the skin of a patient so that the distal end of the needle is in communication with the vascular system of the patient; (3) unlocking the locking means; (4) removing the obturator from the first lumen, the second lumen, the third lumen, the fourth lumen and the fifth lumen; (5) engaging the closure means so as to close off the third lumen; (6) removing the cap from the proximal body element; and (7) disengaging the closure means so as to open up the third lumen; whereby access to the vascular system of the patient will be provided through the first, second, third and fourth lumens.

BRIEF DESCRIPTION OF THE DRAWINGS

These and other objects, features and advantages of the present invention will be apparent from the following detailed description of the preferred embodiments thereof, which are to be considered in conjunction with the accompanying drawings in which:

FIG. 1A is a front axial view of an implantable access device of the present invention;

FIG. 1B is a top plan view of an implantable access device of the present invention;

FIG. 1C is a side elevational view of an implantable access device of the present invention;

FIG. 1D is a bottom plan view of an implantable access device of the present invention;

FIG. 1E is a rear axial view of an implantable access device of the present invention;

FIG. 2A is a cross-sectional view of the implantable access device of FIG. 1B, taken through the line A-A', with a corresponding needle (or cannula)/obturator assembly not yet inserted;

FIG. 2B shows the access device of FIG. 2A, but with the corresponding needle (or cannula)/obturator assembly inserted and the obturator in the process of being removed;

FIG. 9 is a top plan view of a single needle (or cannula) hub having two needles (or cannulas) mounted therein;

FIG. 10 is a top plan view of a pair of needle (or cannula) hubs disposed side by side, each of the hubs having one needle (or cannula) mounted therein;

DESCRIPTION OF THE PREFERRED EMBODIMENTS

Figure 3A:
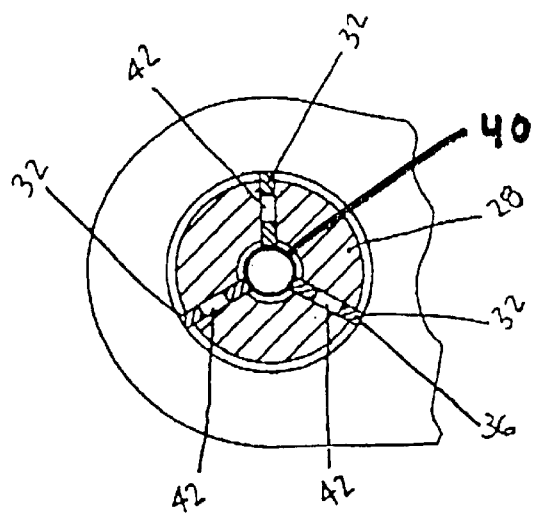
FIG. 3A is a cross-sectional view taken through the line B-B' of FIG. 2B.

Referring to the various figures, wherein like reference numerals represent like parts throughout the several views, it is understood that the device is bilaterally symmetrical through the various cross-sections taken and that corresponding halves of parts shown in cross-section represent cylindrical structures. It is further understood that the present invention contemplates a single implantable access device that accommodates a single needle (or cannula)/catheter fluid passage, or a ganged plurality of such passages, or separate such devices, each accommodating either a single or ganged plurality of such passages.

Turning now to the drawings, FIGS. 1–8 show a dual-line channel embodiment of the implantable access device with corresponding cannula (or needle)/obturator assemblies of the present invention. Access device 10 (FIG. 1B), implantable just under the skin S (FIG. 1C) of a patient, comprises a needle guidance element 12 (FIG. 1C), a catheter locking element 16 (FIG. 1C), and a protective cowling 14 (FIG. 1C) accommodating these and related internal elements. For purposes of this discussion, it is understood that the embodiment of access device 10 contemplates dual passages; however, solely for simplicity of description, the elements will be referred to in the singular, as though only one passage were present.

Anatomical Mounting Plate

Referring back to FIGS. 1A–1E, the mounting plate 60 (FIG. 1C) has a plurality of eyelets 98 (FIG. 1D) for suturing attachment to subcutaneous tissue. As discussed previously, the anatomical mounting plate 60 is attached to access device 10 by means that allow the mounting plate to pivot in relation to the access device. This allows, in sequential hemodialysis sessions a day or two apart, the access device 10, with ganged access to internal catheters, to be pivoted so as to allow needle (or cannula) access at different skin puncture sites while other such sites heal.

Protective cowling 14 (FIG. 1C) has a lower surface 58 (FIG. 1C) accommodating the anatomical mounting plate 60 by means of a rivet 62 (FIG. 1D) being disposed through a lumen 64 (FIG. 1D) of the anatomical mounting plate and further through a mating opening (not shown) in the lower surface of the protective cowling 14.

The arrangement of mounting the protective cowling 14 to the plate 60 allows the mounting plate to pivot relative to the cowling 14. There is a shoulder 66 (FIG. 1C) that acts to restrain the pivot action (i.e., by the plate 60 striking the shoulder 66) to a zone of about 30° (i.e., about 15° clockwise rotation and 15° counterclockwise rotation). Other ranges of pivoting can be used, and other pivoting mounting arrangements suitable for use herein are known in the art.

There is a protective structure 16 (FIG. 1C) surrounding the ends of a catheter. This structure 16 is attached to the cowling 14 and provides a means to retain the catheters to the access device. The catheters may be attached to surrounding tissue so as to generally retain the catheters, and a shroud or other such strain relief elements (not shown) may surround the catheters proximate the access device, as is known in the art, so as to protect the ends of the catheters from undue stress or strain.

Internal Components of the Access Device

Looking now at the individual components of access device 10, FIGS. 1A–1E show an embodiment of the needle guidance entrance 12 (FIG. 1B) of the present invention. This entrance 12 has an inwardly sloped and concave first end bounded by conical ends 18 and 18' (FIG. 1A) such that a rigid implement, such as needle (or cannula)/obturator assembly 20 (FIG. 1B), is guided to either entrance lumen 22, 22' (FIG. 1A) or lateral trough 24 (FIG. 1B). The trough 24 has a rounded cross-section as shown in FIG. 1C, and the lowest surface of the trough is a straight connection between the two entrance apertures 18 and 18' (FIG. 1A). If the implement (e.g., needle or cannula/obturator assembly 20) contacts trough 24, there is no structure or slope to impede the lateral movement of the implement to either aperture 18 or 18'.

FIGS. 2A and 2B show an embodiment of a lock assembly 26 in each channel of the dual lumen access device 10. Lock assembly 26 comprises a silicone rubber plug 28 (FIG. 2A) with a hollow elongated passage 30 (FIG. 2A) therein accommodating an inserted needle (or cannula) 40 (FIG. 2B) with some clearance, and one or more (preferably three, but variable from one to ten or more) radial locking blades 32 (FIG. 2A). The blades 32 can be rectangular in longitudinal cross-section, or tapered as shown in FIGS. 2A and 2B.

Figure 3C:
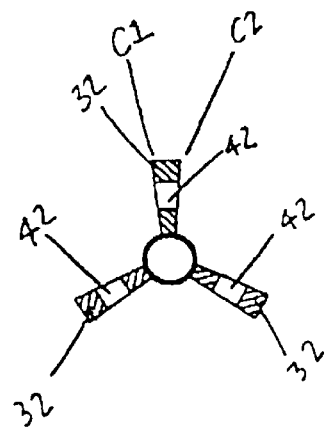
FIG. 3C is a view of an alternate form of the locking blades of FIG. 3A (distorted somewhat for clarity of illustration)
Figure 3B:
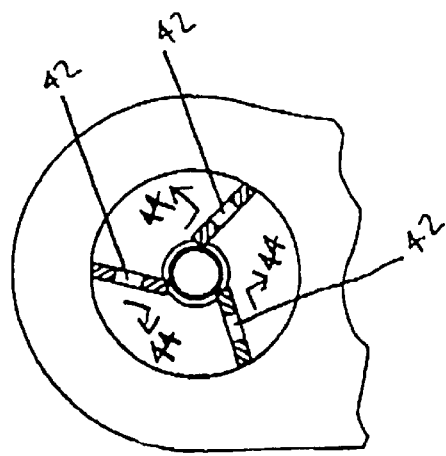
FIG. 3B is the same view as FIG. 3A, but with the needle (or cannula) twisted.

Referring now to FIGS. 2B, 3A and 3B, each blade 32 has an axial-direction-tapered outer edge 34 (FIG. 2B) tapering towards the guidance element entrance 22 (FIG. 1A), and the guidance element 12 has a corresponding taper 36 (FIG. 2B). FIGS. 3A and 3B are cross-sections taken through the line B-B' of FIG. 2B. Each blade 32 also has an inner edge 38 (FIG. 2B) which comprises one or more teeth, preferably of shallow clearance angle, ending in a point or a small length contact with the outer surface of a needle (or cannula) 40 (FIG. 2B). Each blade 32 has holes 42 (FIG. 2B) formed therein, allowing the plug 28 (FIG. 3A) to be continuous and retain the metal blades 32 in relative positions to the rubber body 28 and to each other. FIG. 3A shows the locking blades 32 securely engaging the outer surface of needle (or cannula) 40, locking the needle (or cannula) to the access device 10. FIG. 3B is a cross-sectional view as in FIG. 3A, except showing the effect of twisting the needle (or cannula) 40 so that the blades 32 are not aligned radially to the outer surface of the needle (or cannula). The locking blades 32 pivot about their outer edges 34 (FIG. 2B), and the inner edges 38 (FIG. 2B), and the teeth move away (as at 44 in FIG. 3B) from the outer surface of the needle (or cannula) 40 and thereby provide little retaining force on the needle (or cannula). Twisting the needle (or cannula) 40 while axially withdrawing the needle (or cannula) allows the needle (or cannula) to be extracted from the access device 10 with little force. To accommodate this withdrawing, the cross-section of the blades 32 may be tapered from the outer edges 34 to the inner edges 38. After the needle (or cannula) 40 is withdrawn, the plug 28 and blades 32 return to their original position, as shown in FIG. 3A.

Figure 3D:
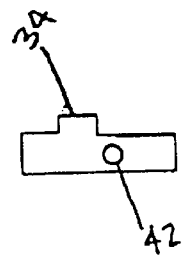
FIG. 3D is a side view of another alternative form of blade design.

Other forms of the blades 32 are shown in FIGS. 3C and 3D. In FIG. 3C, the blades 32 are cross-section tapered (distorted somewhat in FIG. 3C for clarity of illustration) to establish corners C1, C2 as pivot points for accommodating the tilting of the blades, from radial to non-radial alignment, as needle (or cannula) 40 is twisted. FIG. 3D shows a form of blade 32 that has a limited length outer edge 34 compared to the blade length as a whole. The blade 32 can be rectangular in cross-section, or tapered as shown in FIG. 3C. The blade 28 can be contained in the plug 28 without a need for holes, but one or more such holes 42 can be provided, optionally.

FIGS. 1A–1E, 2A and 2B show an embodiment of a protective cowling 14 that defines a space 46 (FIG. 2A) capable of accommodating needle guidance means 48 (FIG. 2A), needle alignment means 50 (FIG. 2B), a cannula seal 92 (FIG. 2A), a flexible valve seal 52 (FIG. 2A), an elastomer 54 (FIG. 2A), and a transition channel 56 (FIG. 2A). The needle (or cannula) and obturator assembly 20 (FIG. 2A) penetrates the locking mechanism 26 (FIG. 2A) and continues through the ring seal 92 (FIG. 2A). This ring seal 92 prevents leakage as the needle (or cannula) 40 is removed after use. The needle (or cannula) and obturator assembly 20 continues to penetrate to the rigid guide elements 50 (FIG. 2B), which force open a slit 53 (FIG. 4A) in the seal 52 (FIG. 2A), as described below. The elastomer 54 (FIG. 4A) surrounds the seal 52. Both elements 52 and 54 are made of elastomeric materials. However, the elastomer of valve seal 52 is more supple, with a lower durometer rating, than that of elastomer 54. The more supple material of valve seal 52 accommodates particles or other small debris that may be attached to the needle (or cannula) and obturator assembly 20 and still provides a good seal.

Figure 4A:
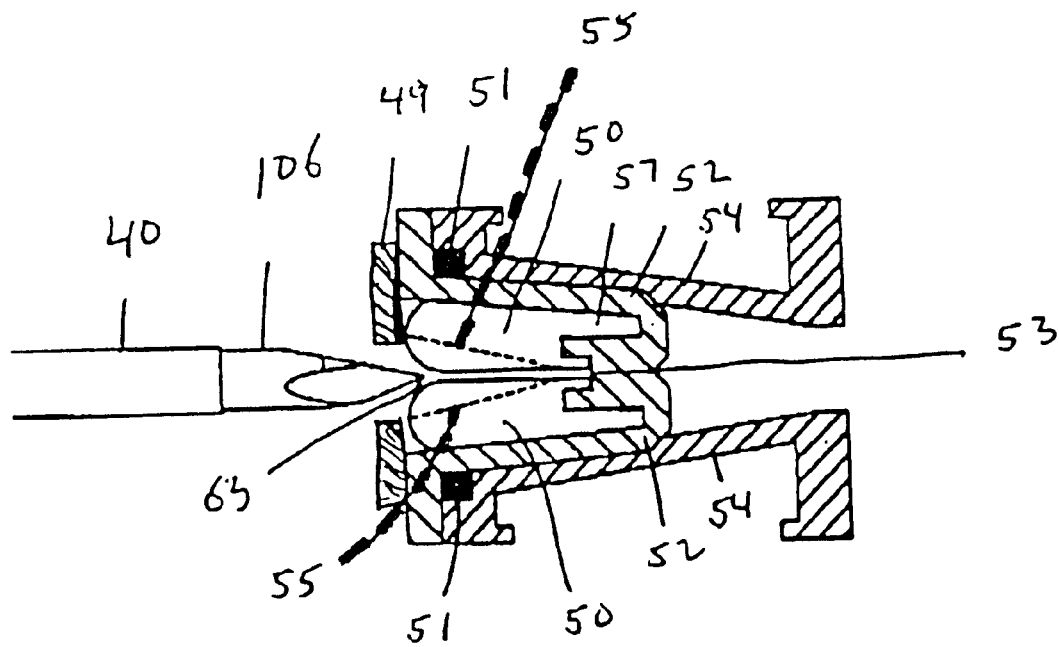
FIG. 4A is a partially cross-sectional view of the valve guides and resilient seal, with the needle (or cannula) and obturator assembly not yet inserted.

FIG. 4A shows the tip of the obturator 106 just before the obturator enters the rigid guides 50. The guides 50 are retained by a retaining disk 49 and the seal 52. The access device 10 also comprises the above-mentioned valve structure, seated between (1) the retaining disk 49 (FIG. 4A) which is in turn held, as shown in FIG. 2B, by an annular shoulder of needle guidance means 48 and by cannula seal 92, and (2) a catheter connector retaining ring 68 (FIG. 2A), held at an annular shoulder 94 (FIG. 2A) of protective cowling 14 (annular shoulder 94 may be provided by a ring portion of cowling 14, or by radial inserts instead of a ring). The valve is maintained in an elongated position, such that it does not dislodge during needle (or cannula) insertion or withdrawal, by a retaining element 96 (FIG. 2A) and the cowling 14.

Figure 4B:
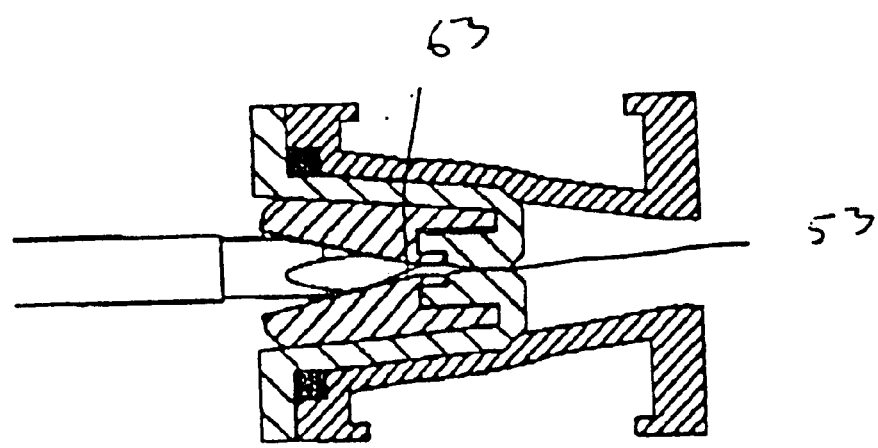
FIG. 4B is the same view as FIG. 4A, but with the needle (or cannula) and obturator assembly being inserted.

Referring back to FIG. 4A, the valve has opposing guide elements 50 with a surface hardened to a point higher than that of the steel used in the obturator 106. These guide elements 50 may be made of ceramic, or may be coated with a hard material such as titanium nitride. The valve seal 52 is formed with a sealing portion with a slit 53 (FIG. 4A) that is axially aligned with the obturator 106. The guide elements 50 have extensions 57 (FIG. 4A) that seat in apertures in the sealing portion of valve seal 52. This intimate contact of the guide elements 50 and the seal 52 compels the slit 53 to follow the ends 57 (FIG. 4A) of the guide elements. When these ends 57 open, the slit 53 opens, as shown in FIG. 4B. There is a retaining ring 51 (FIG. 4A) encircling the guide elements 50, distal from the slit 53. This ring 51 acts as a pivot point when the guide elements 50 open. The hardened surfaces of the guide elements 50 are tapered, as shown at 55, toward the slit 53 and guide the needle (or cannula) and obturator assembly 20 to the slit.

Referring now to FIG. 4B, the outer diameter of the needle (or cannula) 40, or the obturator 106, contacts the guide assembly and opens the guide elements 50 before a point 63 of the needle (or cannula) and obturator assembly 20 reaches the slit 53. As illustrated, the guide elements 50 pivot about the retaining ring 51. The elastomer material 54

(FIG. 4A) substantially surrounds the seal 52. As mentioned above, the elastomer 54 and the seal 52 are constructed with different durometer levels that separate the sealing attribute from the forcing means. As the guide elements 50 open, both the elastomer 54 and seal 52 resist the opening and, as the needle (or cannula) and obturator assembly 20 penetrates completely through the slit 53, the elastomer 54 and the seal 52 conform around the needle (or cannula) and obturator assembly 20 to form a seal thereto. The elastomers are providing an inward radial force urging the slit closed. The obturator 106 may thereafter be removed, and the elastomer 54 forces the seal 52 to conform to the outer cylindrical surface of the needle (or cannula) 40 to form a seal thereto. When the needle (or cannula) 40 is thereafter removed, the slit closes by the elastomer action of the materials 54 and 52.

Figure 5A:
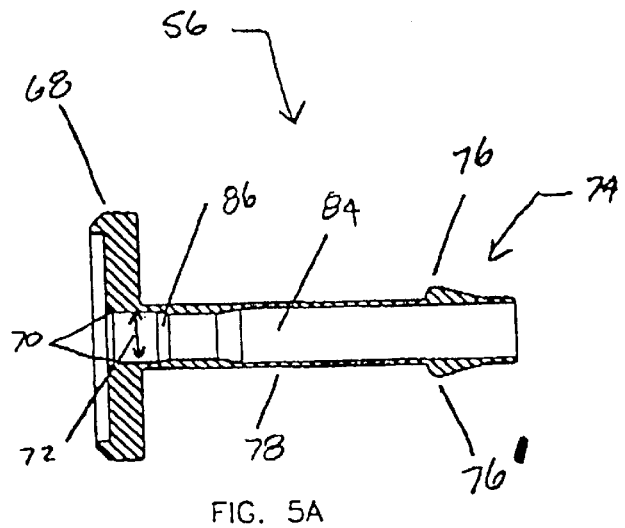
FIG. 5A is a cross-sectional view of a transition channel of an implantable access device of the present invention.

FIG. 5A shows an embodiment of one of the matching pair of connecting transition channels 56 shown in FIGS. 2A and 2B. These elements 56 provide a flanged end 68 that is retained in the cowling 14. The fully inserted needle (or cannula) 40 matches, and mates with, a channeled surface 70 (FIG. 5A). The internal diameter 72 matches that of the needle (or cannula) 40 and the transition channel 56 provides fairing for a transition from the needle (or cannula) internal diameter to the internal diameter of the catheter. This construction minimizes any flow discontinuities. The end 74 (FIG. 5A) of the transition element 56 has flared extensions 76 and 76'. The catheter slips over these extensions and is retained thereby, as well as by the element 16 (FIG. 2A). As seen in FIG. 5A, the transition channel 56 has a barrel segment 78.

Referring back to FIG. 2A, the retaining flange 68 is disposed within space 46 of protective cowling 14, such that it is held at annular shoulder 80 of protective cowling 14, and further, such that barrel segment 78 (FIG. 5A) is disposed within lumen 82 (FIG. 2A) of protective cowling 14. Catheter connector retaining flange 68 itself defines an annular shoulder capable of accommodating valve seating means 54 (FIG. 2A). The transition channel 56 further defines an axial lumen 84 (FIG. 5A) having disposed, at some point along its length, a needle stop 86, shown here as a conical narrowing of lumen 84, although other designs are contemplated. It is important to the purposes of this invention, however, that all transitions in lumen diameter be sufficiently gradual as to inhibit damaging delicate blood cells.

Flow in the Access Device(s)

Focusing again on FIGS. 2A and 2B, it is seen that the internal passage of access device 10 can be very short, that a generally straight flow path is established, and that the inner diameter of the needle (or cannula) 40 can be larger than is conventional. These factors reduce the flow resistance and allow the access device to accommodate high fluid flow rates with low shear (i.e., lower than state of the art shear rates, generally, and with short blood residence times at the highest shear rate zones), and to limit other deleterious effects as to the fluid passing through the access device.

The needle (or cannula) and obturator assembly 20 (discussed in more detail in connection with FIGS. 6A, 6B, 6C, 7A, 7B and 7C below) has an interior obturator nail 106 (FIG. 6A), and a surrounding needle (or cannula) sheath 40 that can be of very thin wall construction. Thus, for a standard needle (or cannula) outer diameter of 0.072 inch, an inner diameter of 0.0673 inch (compared to a standard of 0.064 inch) can be provided because of obturator reinforcement. This 0.0033 inch difference in inner diameters affords, approximately, a greater than 20% decrease in flow resistance. The obturator 106 (FIG. 6A) also prevents a coring, or cookie cutter, effect that can arise from using a hollow needle (or cannula) for subcutaneous accessing.

Needle/Obturator Assembly

Figure 6A:
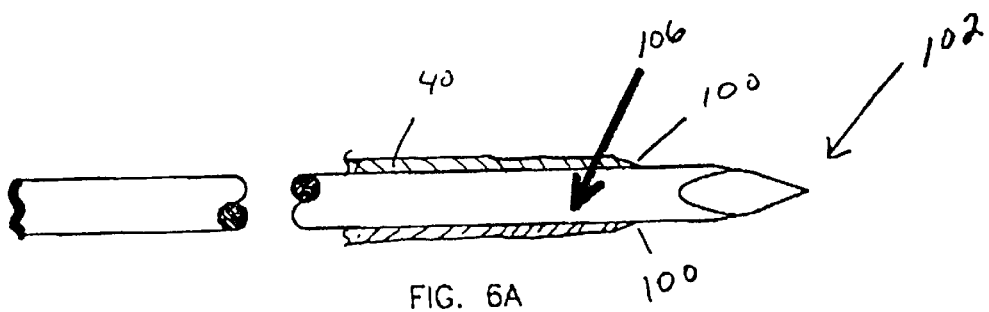
FIG. 6A is a partial side elevational view of the distal end of the needle (or cannula) and obturator assembly of the present invention.
Figures 6B, 6C:
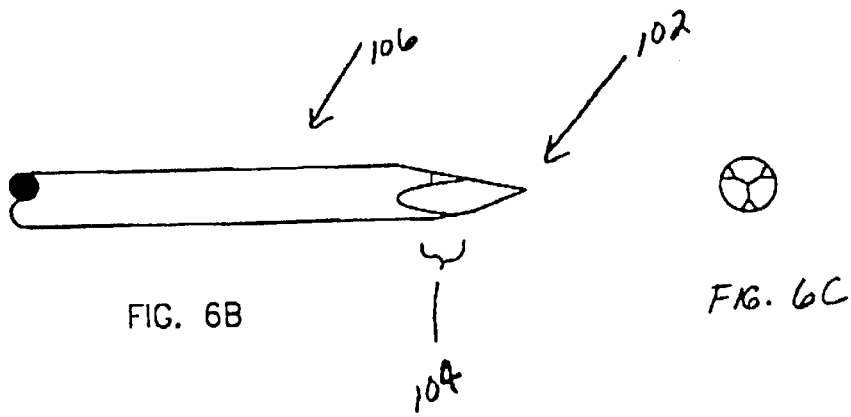
FIG. 6B is a side elevational view of the obturator of FIG. 6A, rotated 90 degrees about its longitudinal axis.
FIG. 6C is a front end view of the leading tip of the obturator shown in FIGS. 6A and 6B.

FIGS. 6A, 6B, and 6C show the piercing end of the needle (or cannula) and obturator assembly 20, with the needle (or cannula) 40 having a wall end 100 (FIG. 6A) that is beveled so as to blend with the obturator 106 and thereby lessen the resistance to penetrating tissue and the access device. The needle (or cannula) end 100 also seats firmly on the corresponding conical stop 86 (FIG. 5A) within axial lumen 84 of transition channel 56. Obturator tip 102 has a distal end with multiple facets (preferably three) as shown in FIGS. 6A, 6B and 6C. These facets may be concave to provide sharper cutting edges. The portion 104 (FIG. 6B) of the point, which blends the cutting edges with the outer surface of the obturator, is dulled by providing a greater number of facets, thereby providing a smooth transition from point and cutting edges to cylindrical form.

Obturator cutting for skin penetration is done along meeting lines of distal end facets, rather than solely or primarily at the distal point. This reduces pain to the patient, since the cut is over a short length and does not tear skin over a significant length. However, when the obturator point enters entrance lumen 22 (FIG. 1A) of access device 10 and passes therethrough, it does not cut, score or otherwise mar the internal wall of the lumen or the interiors of the locking and sealing components of access device 10 that extend from the lumen.

The dulled section 104 (FIG. 6B) does not score the internal passage of the access device. Once the needle (or cannula) and obturator assembly 20 is fully inserted in access device 10, and its needle (or cannula) shell 40 is locked in and sealed, obturator 106 can be withdrawn so as to leave a smooth flow path beginning in a passageway 108 (FIG. 8C) of a hub structure 110 (FIG. 8C), and continuing therein to a smooth blending with a passageway 112 (FIG. 8C) of hub structure 110, and continuing through the full length of the needle (or cannula) 40, and continuing through the length of the transition channel 56 (FIG. 2A), and then into the implantable catheter within the patient.

Figure 7A:
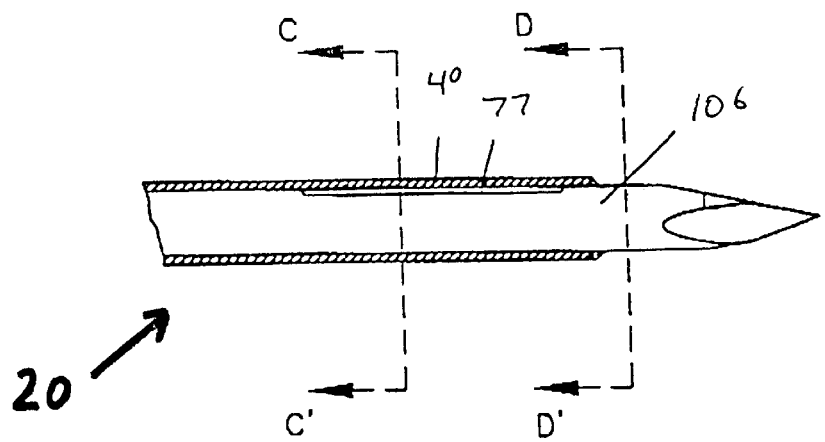
FIG. 7A is a partially cross-sectional view of the distal end of the needle (or cannula)/obturator assembly of the present invention.
Figures 7B, 7C:
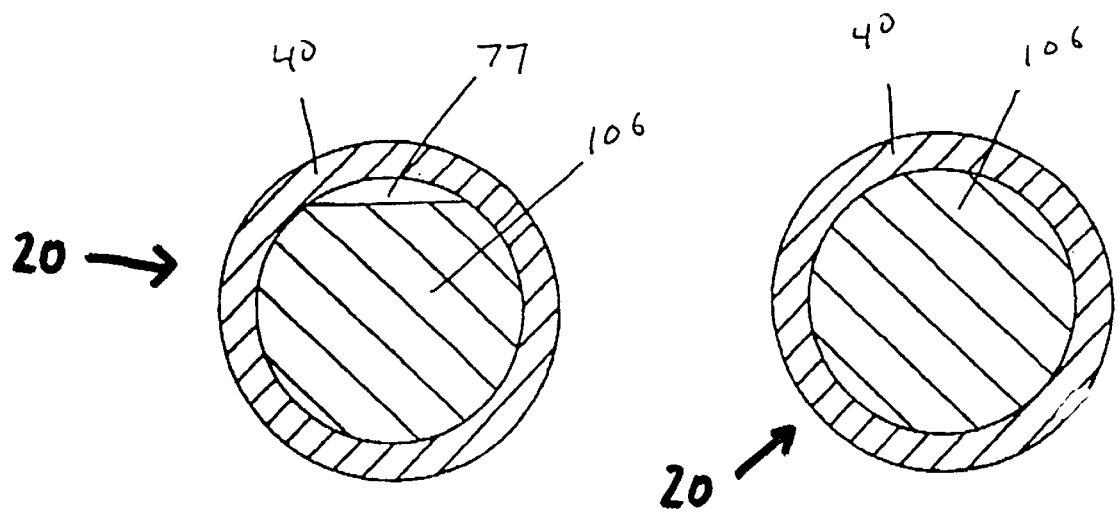
FIG. 7B is a cross-sectional view of the needle (or cannula)/obturator assembly, taken through the line C-C' of FIG. 7A.
FIG. 7C is a cross-sectional view of the needle (or cannula)/obturator assembly, but taken through the line D-D' of FIG. 7A.

FIG. 7A shows the needle (or cannula) and obturator assembly 20 with a chordal channel 77 cut into the obturator 106. The cross-section of FIG. 7B shows the chordal channel 77, as compared to FIG. 7C showing the uncut obturator 106. The passageway provided by chordal channel 77 allows air to escape while inserting the needle (or cannula) and obturator assembly 20.

Extracorporeal Needle (or Cannula) Hub

Figure 8A:
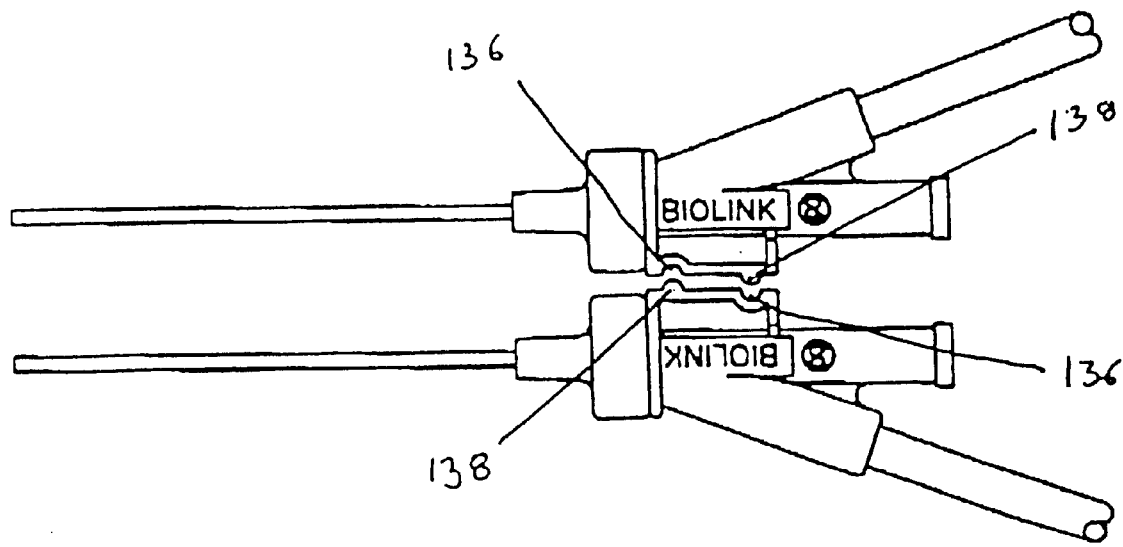
FIG. 8A is a side elevational view of two extracorporeal needle (or cannula) hubs of the present invention being combined.
Figure 8B:
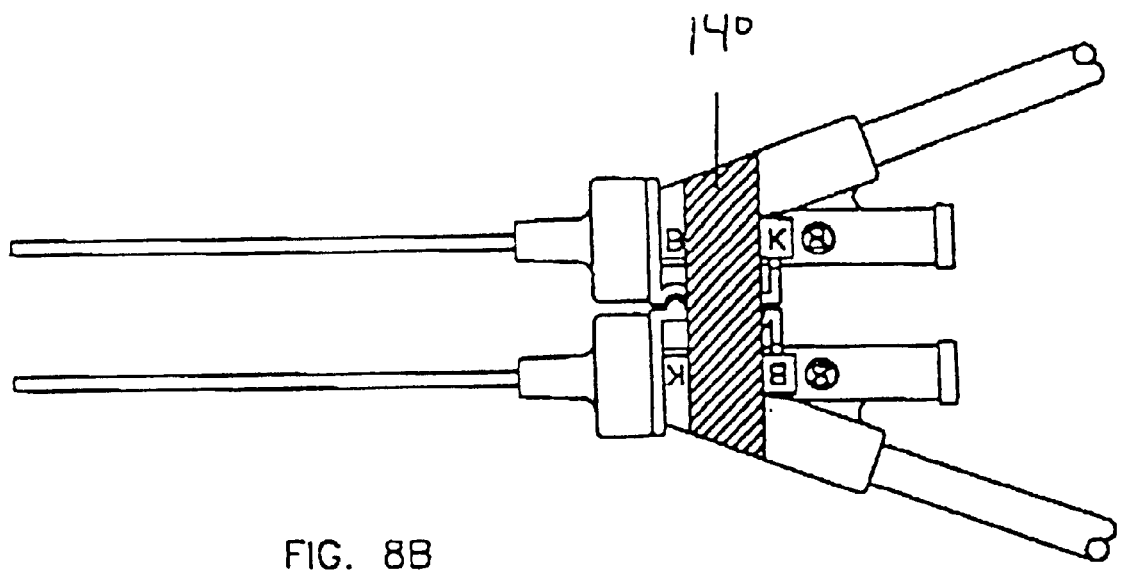
FIG. 8B is a side elevational view of the two extracorporeal needle (or cannula) hubs of FIG. 8A attached to one another.
Figure 8C:
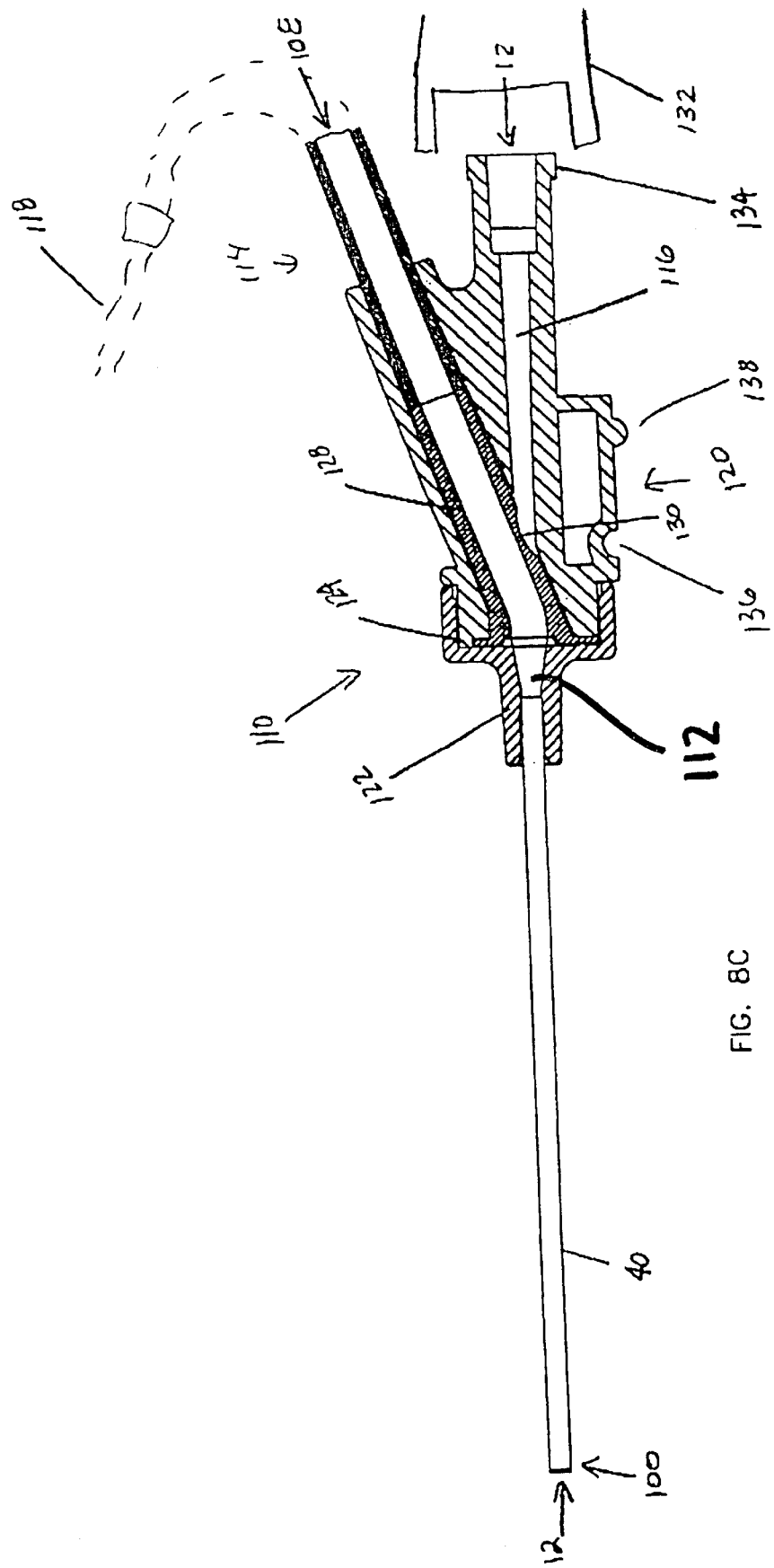
FIG. 8C is a cross-sectional view of an extracorporeal needle (or cannula) hub of the present invention.

FIG. 8C shows an extracorporeal hub structure 110 attached to the proximal end of needle (or cannula) 40. The hub structure 110 comprises a hub body 114 defining a Y-shaped arrangement of three internal passageways 108, 116, and 112. Passageways 108 and 112 are provided for connection to a blood line 118 from a dialysis machine. Passageways 116 and 112 are provided for accommodation of obturator 106, such that a long extension of the obturator, or an extension rod or linkage connected thereto, can be accommodated (in either case with an operating handle that allows axial pushing/pulling of the obturator 106, and the needle/obturator assembly 20). It is contemplated that each hub structure 110 will comprise two mating mirror-image halves (one of which is shown in FIG. 8C) which are formed out of plastic or metal or ceramic and thereafter assembled together by ultrasonic welding, adhesives, solvent bonding, or other appropriate means. Alternatively, each hub structure 110 could be molded or cast as a single piece.

Needle cannula 40 terminates within collar 122 (FIG. 8C) and is bonded thereto. Collar 122 is in turn securely attached to operating handle (or hub body) 114 such that collar 122 abuts a retaining lip 124 of operating handle (or hub body) 114. Thus, rotating the hub structure as a whole rotates the needle (or cannula) 40 for unlocking the needle (or cannula) 40 within access device 10, as described above. Alternatively, an inserted sleeve (not shown) with dial access (also not shown) can provide a similar control. Passageway 116 (FIG. 8C) flares outward at its proximal end so as to form a control entry 126 for insertion of obturator 106.

Flexible insert 128 (FIG. 8C) is disposed within passageway 108 so that it defines a gradual bend in passageway 108 of sufficient arc to align passageway 108 with passageway 112. Insert 128 has a sealed plug portion 130 (FIG. 8C) closing off passageway 116 where passageway 116 communicates with passageway 108. Sealed plug 130 is pierced by the obturator 106 on initial insertion of the obturator, thereby allowing communication of passageway 116 with passageway 112.

Passageways 108, 116, and 112 have smooth internal flow path radii in the flow path section. Generally, passageways 108, 116, and 112 (as well as control entry 126, cannula 40, obturator 106, and entrance lumens 22 of access device 10) are of round form, preferably, but they can also be of square or triangular or oval form, if desired, or some other shape.

When the obturator 106 is removed from hub structure 110 after subcutaneous insertion of the needle/obturator assembly 20 into access device 10, but prior to the start of the treatment session, sealed plug portion 130 self-seals the communication between passageway 112 and passageway 116, thereby preventing fluid flow out through passageway 116 during treatment. To further ensure that fluid is not lost through passageway 116 during treatment, a cap 132 (FIG. 8C) can be secured to operating handle (or hub body) 114 at control entry 126 by means of a lip 134, which may optionally take the form of a screw thread or other shape capable of cooperating with the internal shape of the cap 132 so as to ensure a secure fit of the cap to operating handle (or hub body) 114.

Operating handle (or hub body) 114 is provided with locking means having a joining surface 120 (FIG. 8C) that forms alternating recesses 136 (FIG. 8C) and protrusions 138 such that, when two like hub structures 110 are used with an access device 10 having at least two entrance lumens 22, the respective joining surfaces of the hub structures 110 may be matingly fitted together, as shown in FIG. 8A, so as to prevent rotational movement of either hub structure or their related needles (or cannulas) 40 when the needles (or cannulas) are inserted into the access device 10. Moving of either hub structure away from the other will allow rotational movement of either hub structure 110, as necessary for withdrawal of needles (or cannulas) 40. FIG. 8B show a wrapping 140 around the two hub structures 110 which will retain each to the other in a locking fashion.

Variants

There can be non-annular forms of the locking device. For example, the parts shown as annular pieces or arrays in FIGS. 2–3 can be part-annular or non-annular.

The locking blades can be of various other forms, e.g., blocks, balls, rollers, etc. Springs, e.g., coil or leaf or other types, can be used to assist locking or unlocking actions. The locking action can involve inscribing a needle (or cannula) outer surface, holding it by friction, or geometric blocking of a locking element with a rib or other protrusion on such surface.

The plug seal and/or its closing bias means can be of various forms and of different materials as are known in the art.

Additional Constructions

Referring next to FIG. 9, it will be seen that a single hub structure 200 can be formed which has two needles (or cannula) 40 mounted therein, in parallel disposition. The internal construction of hub structure 200 is generally similar to the internal construction of hub structure 110 (FIG. 8C), except that the internal construction of hub structure 200 is adapted to service a pair of needles (or cannulas) 40 rather than just a single needle (or cannula) 40. Thus, in brief, with hub structure 200, each of the needles (or cannulas) 40 is connected, at its proximal end, to a hub passageway 112. Each of the hub passageways 112 is, in turn, connected to a flexible insert 128. Each of the flexible inserts 128 is, in turn, connected to (1) a blood passageway 108, and (2) an obturator passageway 116 (via sealed plug portion 130).

As stated above, the single hub structure 200 has two needles (or cannulas) 40 mounted therein. Thus, by manipulation of the single hub structure 200, the two needles (or cannulas) 40, with their associated obturators 106 (not shown in FIG. 9), may be advanced simultaneously for engagement with the lumens 22, 22' of access device 10.

In operation of the needle (or cannula) and obturator assembly shown in FIG. 9, two complete needle (or cannula) and obturator units are advanced substantially simultaneously through the skin of a patient and into the entrance lumens 22, 22' of access device 10. When the needles (or cannulas) 40 are fully inserted in the access device, their associated obturators (not shown) are withdrawn and the needles (or cannulas) serve as passageways extending between access device 10 and the hub structure 200. Fitted to the hub structure 200 are inlet/outlet fixtures 202 to permit flow of fluid into and out of the hub structure 200, and hence into and out of access device 10.

Of course, with the needle (or cannula) and obturator assembly of FIG. 9, it is not possible to rotate its two needles (or cannulas) 40 simultaneously about each one's own longitudinal axis, in the manner necessary to release the needles (or cannulas) 40 from locking blades 32 of lock assembly 26 (FIG. 3B). Thus, with the needle (or cannula) and obturator assembly of FIG. 9, it is necessary to omit lock assembly 26 from access device 10, or to provide some other type of lock assembly compatible with the needle (or cannula) and obturator assembly of FIG. 9.

As is shown in FIG. 10, the hub structure 200 may also comprise separate first and second hub bodies 205, 205', each hub body 205, 205' having fixed therein one of the needles (or cannulas) 40. Each of the hub bodies 205, 205' includes the hub passageway 112, flexible insert 128, blood passageway 108 and obturator passageway 116 discussed above, but not shown in this figure.

In the embodiment shown in FIG. 10, the two hub bodies 205, 205' may be manipulated individually.

If it is preferred to operate the two hub bodies 205, 205' simultaneously, the hub bodies 205, 205' may be connected together before starting the insertion process, as by encircling the hub bodies 205, 205' with a wrapping 210 (FIG.

Figure 12:
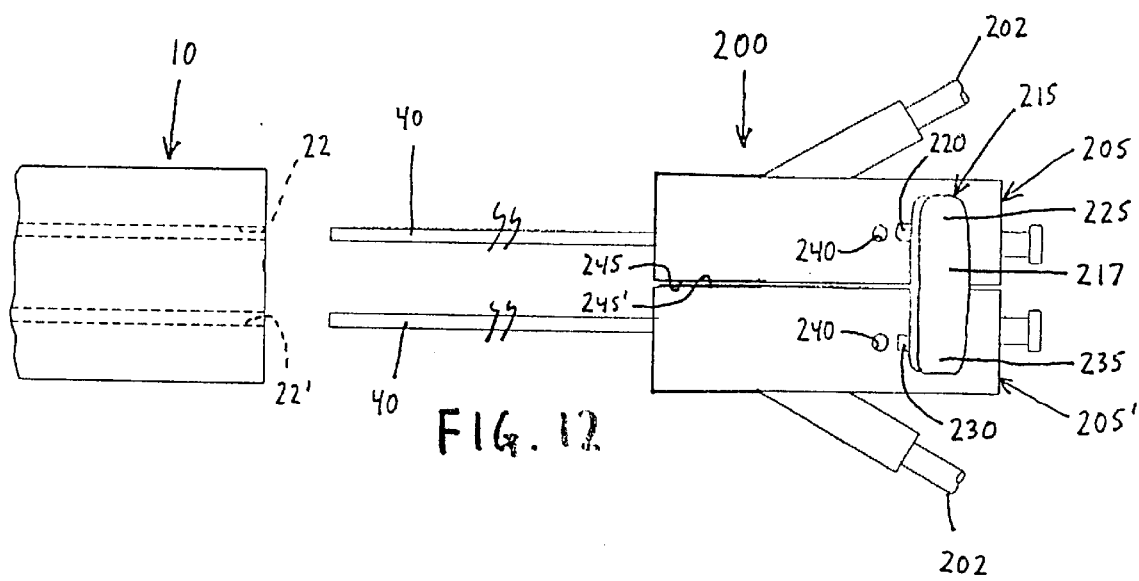
FIG. 12 is similar to FIG. 11, but illustrates an alternative structure for fixing the two needle (or cannula) hubs together.

11), such as tape or the like. Alternatively, the hub bodies 205, 205' may be connected together by a mechanical interlock means 215 (FIG. 12), such as a bar or link 217 having a first protuberance 220 proximate a first end 225 of the link 217 and a second protuberance 230 proximate a second end 235 of the link 217. Each of the hub bodies 205, 205' is in turn provided with a recess 240 for receiving one of the protuberances 220, 230, preferably in "snap-in" fashion, so as to lock the two hub bodies 205, 205' to the link 217 and, thereby, to each other. Thus, the hub bodies 205, 205' may be connected together and advanced in unison toward the access device lumens 22, 22'.

Alternatively, the hub bodies 205, 205' may be advanced independently of one another and, after full insertion of the two needles (or cannulas) 40 into access device lumens 22, 22', be connected together in the manner discussed above.

Figure 11:
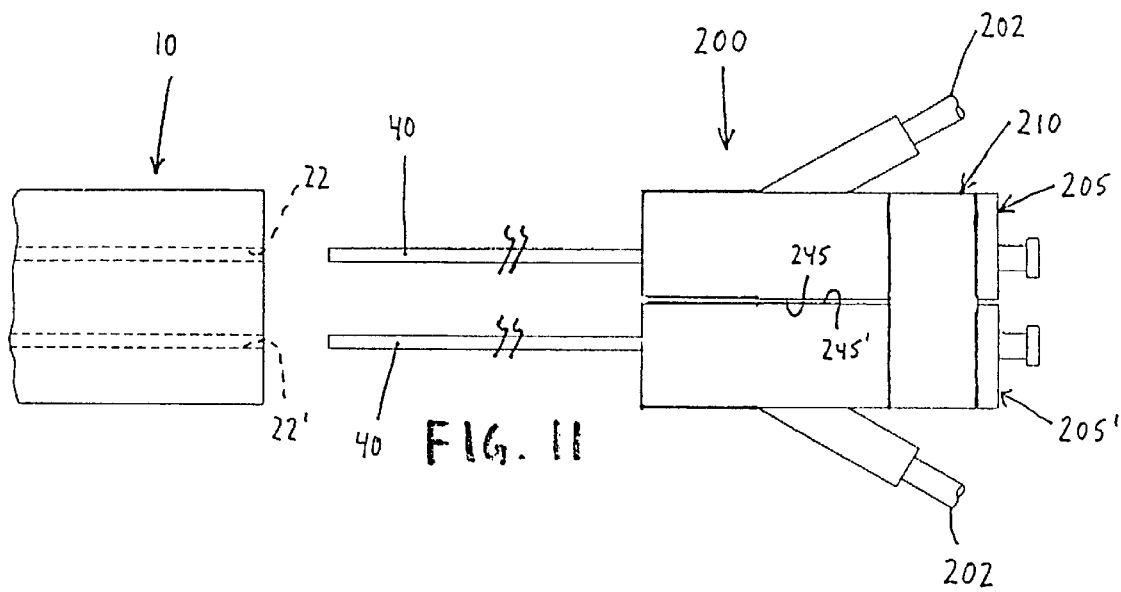
FIG. 11 is a top plan view of the pair of needle (or cannula) hubs shown in FIG. 10, but fixed together.

The hub bodies 205, 205' may be provided with flat sides 245, 245' (FIGS. 10-12), such that nesting together of the two hub bodies, with their needles (or cannulas) 40 in parallel disposition, is easy to obtain.

Figure 13:
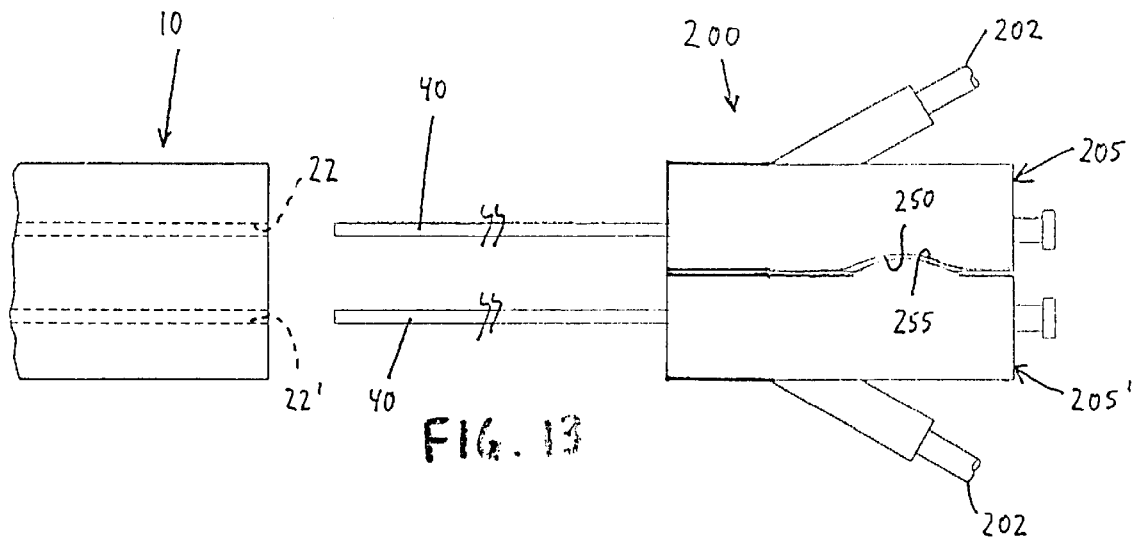
FIG. 13 is similar to FIG. 10, but illustrative of a pair of needle (or cannula) hubs shaped complimentary to each other so as to facilitate matching and joining of the same.
Figure 14:
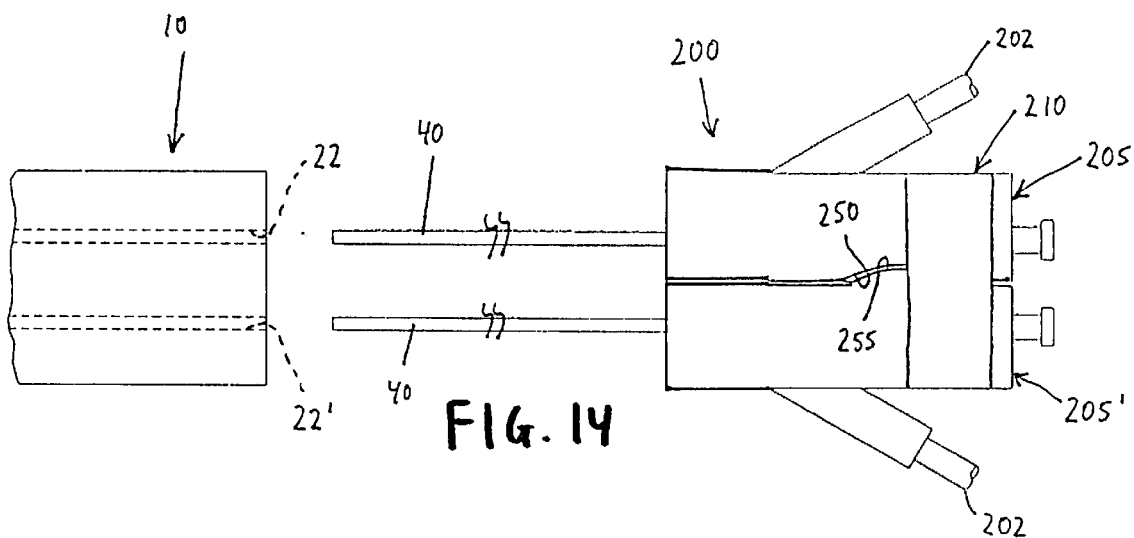
FIG. 14 is similar to FIG. 13, but shows the two needle (or cannula) hubs joined and fixed together.
Figure 15:
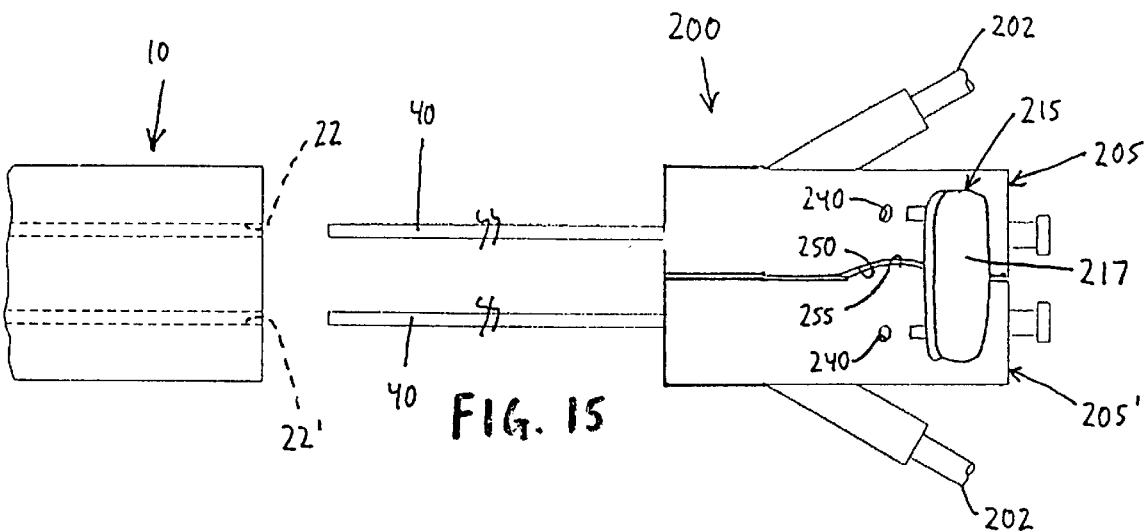
FIG. 15 is similar to FIG. 14, but shows an alternative means for fixing the two needle (or cannula) hubs together.

Alternatively, to assist in correct side by side positioning, the two hub bodies 205, 205' may be provided with non-flat surfaces complimentary to each other, such as the concave and convex surfaces 250, 255 shown in FIGS. 13–15. Complimentarily configured surfaces 250, 255 provide for snug nesting of hub bodies 205, 205'. If desired, hub bodies 205, 205' may also be secured together with the wrapping 210 (FIG. 14) or the mechanical interlock means 215 (FIG. 15). Again, such connection may be effected either before the needles (or cannula) 40 have been advanced into lumens 22, 22' of access device 10 or, alternatively, after completing the insertion process.

In another alternative embodiment (FIG. 16), the hub bodies 205, 205' are provided with surface configurations for interengaging and interlocking with one another. In the embodiment shown in FIG. 16, for example, the first hub body 205 is provided with a first recess 260 and a first projection 265. The second hub body 205' is provided with a second recess 270 and a second projection 275. The first projection 265 is generally axially slidable into the second recess 270, and the second projection 275 is generally axially slidable into the first recess 260. Each of the projections is retained in the recess in which it is disposed so as to fix the first hub body 205 to the second hub body 205'.

Figure 16:
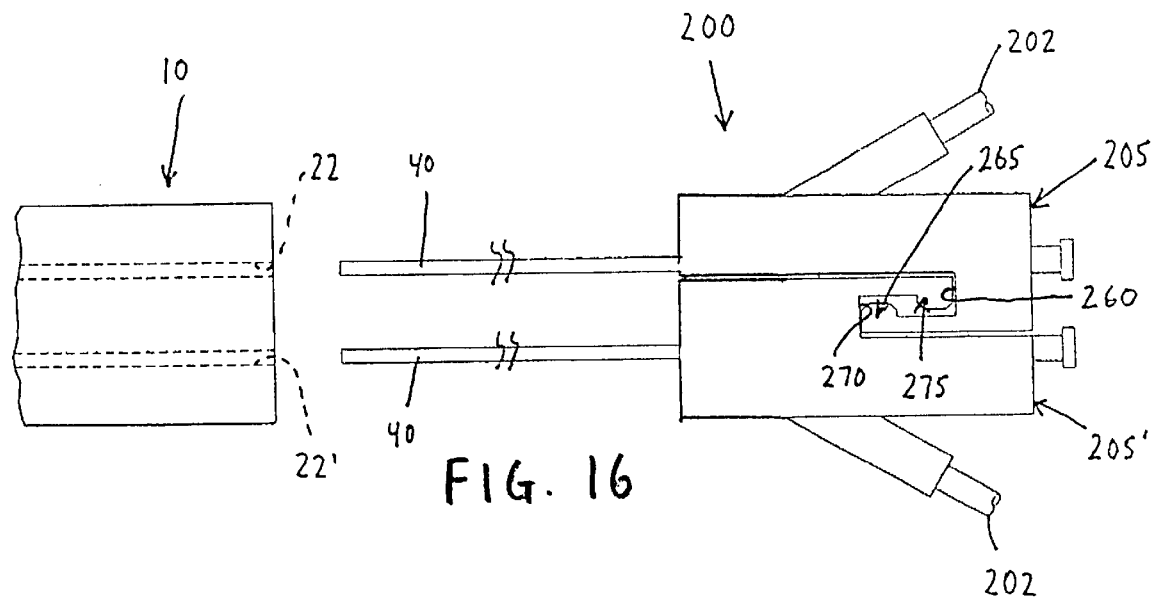
FIG. 16 is a top plan view of a pair of needle (or cannula) hubs shaped complimentarily to each other and such as to fix one to the other without the need of additional fixing structure.

In operation of the assemblies shown in FIGS. 10, 13 and 16, the hub bodies 205, 205' may be connected together, as illustrated in FIGS. 11, 12, 14, 15 and 16, prior to insertion and used in the manner described above.

Alternatively, with these assemblies, the hub bodies 205, 205' may be inserted into the access device 10 individually and then connected together after the needles (or cannulas) 40 are fully inserted. In the embodiment illustrated in FIG. 16, requiring sliding axial movement of one hub body relative to the other hub body to lock the two hub bodies together, typically a first of the units is fully inserted in the access device 10 and then the second of the units is slid toward full insertion and slidingly locked to the first unit.

It will, of course, be appreciated that where the two hub bodies 205, 205' are connected together in the manner illustrated in FIGS. 11, 12, 14, 15 and 16, regardless of whether they are connected together prior to insertion or after insertion, the two hub bodies 205, 205' will be disconnected from one another prior to withdrawal, whereby the needles (or cannulas) 40 may each be rotated about its own individual axis so as to release the needle from locking blades 32 of lock assembly 26 (FIG. 3B). In this respect it will be appreciated that with the embodiment shown in FIG. 16, hub elements 260, 265, 270 and 275 will be configured so as to permit sufficient axial rotation of the two hub bodies 205, 205' relative to one another, even when joined in the manner shown in FIG. 16, to permit a needle (or cannula) 40 to be released from its associated locking blades 32. Alternatively, with the embodiment shown in FIG. 16, lock assembly 26 could be omitted from access device 10, or some other type of lock assembly compatible with the embodiment shown in FIG. 16 could be used.

Figure 17:
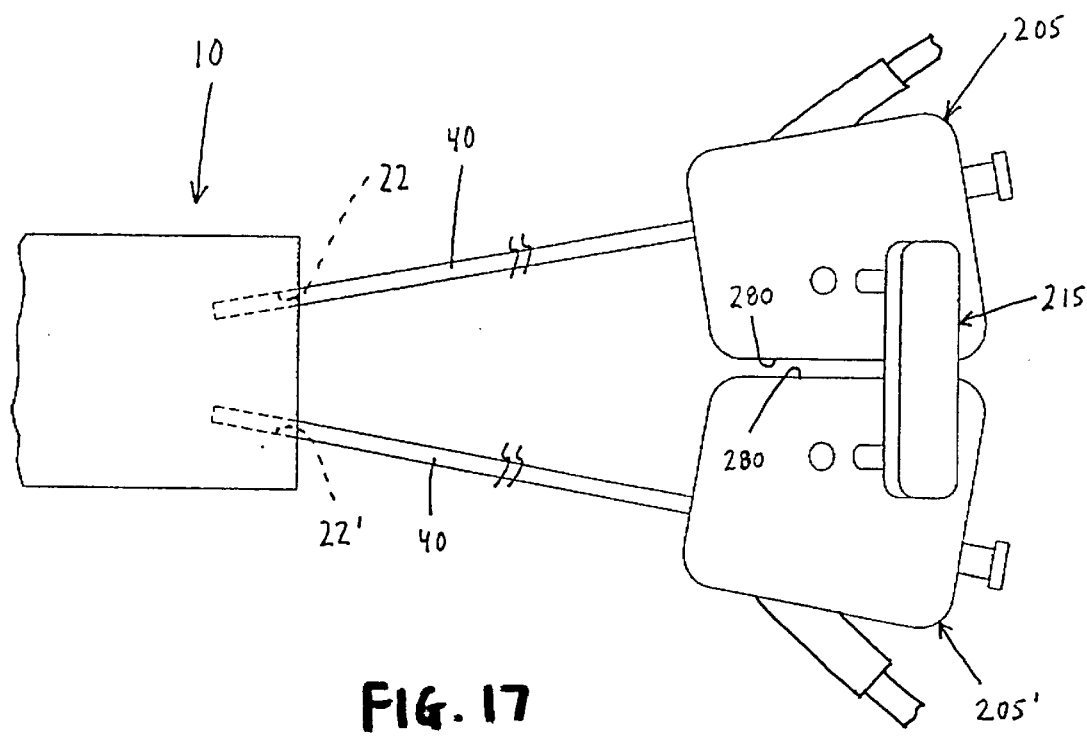
FIG. 17 is similar to FIG. 12, but illustrative of two needle (or cannula) and obturator hubs being shaped to adjoin each other, and adapted to be fixed to each other, so that the two needles (or cannulas) extend in non-parallel relation to each other when the two hubs are joined.

In some instances, the lumens 22, 22' of the access device 10 are not parallel, but rather, incline toward one another (FIG. 17). For such situations, the hub bodies 205, 205' may be provided with flat sides 280 which are angled with respect to the axes of the lumens (FIG. 17), and thereby angled with respect to the axes of the needles (or cannulas) 40. Such hub bodies may be linked together similarly to the hub bodies of FIG. 12, e.g., with the mechanical interlock means 215, although the linking must generally be undertaken after the needles (or cannulas) 40 have been fully inserted into the lumens 22, 22'. One advantage of the embodiment shown in FIG. 17 is that once needles (or cannulas) 40 have been inserted into lumens 22 and hub bodies 205, 205' have been attached together, the needles (or cannulas) will resist withdrawal from access device 10 even if lock assembly 26 were to fail.

There is thus provided means for limiting movement of either hub body or their related needles (or cannulas) after the needles (or cannulas) have been placed in the access device.

In still another alternative embodiment, shown in FIGS. 18–23, the needle (or cannula) and obturator assembly 20 may comprise a hub structure 300. Hub structure 300 in turn comprises a pair of mirror-image hub bodies 305, 305'.

Figure 18:
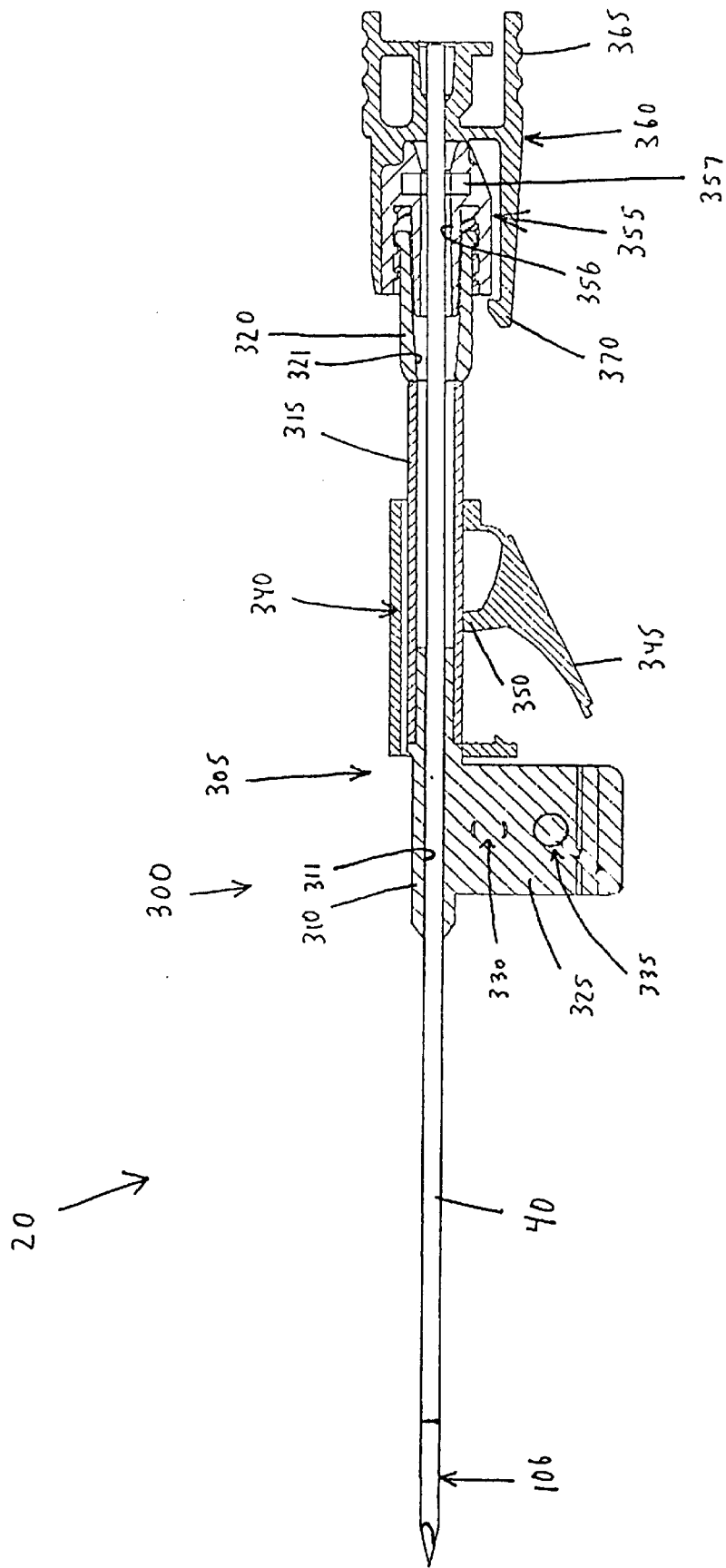
FIG. 18 is a sectional, in part elevational, view of an alternative form of needle (or cannula) and obturator assembly formed in accordance with the present invention.
Figure 19:
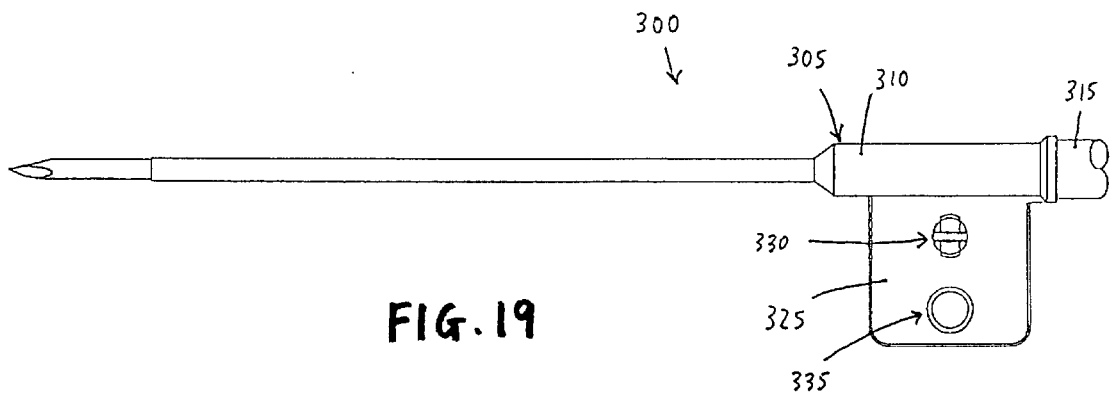
FIG. 19 is a top plan view of the distal portion of the needle (or cannula) and obturator assembly shown in FIG. 18.
Figure 20:
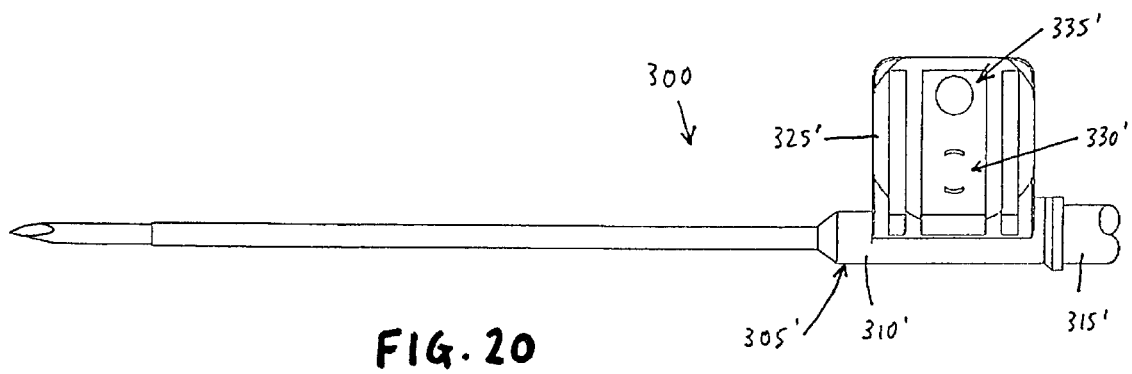
FIG. 20 is a bottom plan view of another needle (or cannula) and obturator assembly which is a mirror-image of the assembly shown in FIG. 19.
Figure 21:
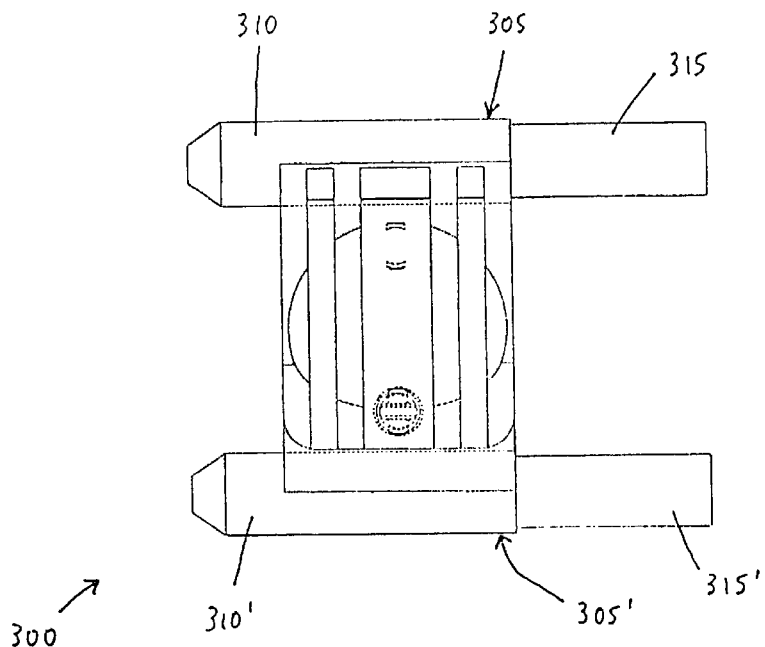
FIG. 21 is a top partial plan view of two needle (or cannula) and obturator assemblies of the type shown in FIGS. 19 and 20 fixed together.
Figure 22:
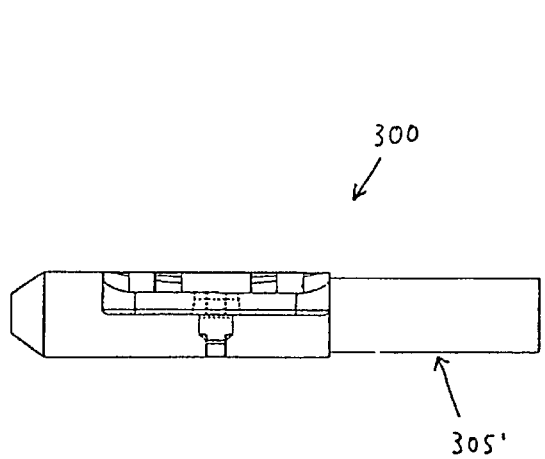
FIG. 22 is a side elevational view of the two joined hubs of FIG. 21.
Figure 23:
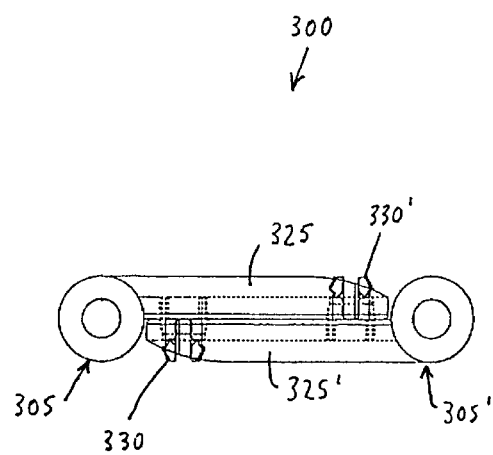
FIG. 23 is a front elevational view of the two joined hubs of FIG. 21.

As seen in FIG. 18, hub body 305 generally comprises a distal body element 310 having a lumen 311, the hollow needle (or cannula) 40 mounted to the distal end of distal body element 310 so that the lumen of the needle communicates with body lumen 311, a hollow compressible tube 315 mounted to the proximal end of distal body element 310 so that the lumen of the tube communicates with body lumen 311, and a proximal body element 320, having a lumen 321, mounted to the proximal end of compressible tube 315 so that the lumen of the tube communicates with body lumen 321.

Distal body element 310 is provided with an outwardly-extending flange 325 having a protuberance 330 and an aperture 335. The two hub bodies 305, 305' are rotatable about their longitudinal axis so as to bring the two flanges 325, 325' into abutting relationship with one another (FIGS. 21–23), with the first protuberance 330 being received in snap-in fashion by the second aperture 335', and the second protuberance 330' being received in snap-in fashion by the first aperture 335, so as to lock the two flanges 325, 325' together, in order to lock the two hub bodies 305, 305' together.

A snap lock 340, comprising a finger seat 345 and a ram 350, is disposed about compressible tube 315. A cap 355, including a lumen 356 closed off by a septum 357, is removably secured to the proximal end of proximal body element 320, e.g., with a screw mount.

The needle (or cannula) and obturator assembly 20 shown in FIGS. 18–23 also comprises the obturator 106. Obturator 106 has a snap lock 360 (FIG. 18) fitted to its proximal end. Snap lock 360 comprises a finger seat 365 and a catch 370.

The needle (or cannula) and obturator assembly 20 of FIGS. 18–23 may be used as follows. With the assembly in the configuration shown in FIG. 18, i.e., with obturator 106 extending through needle (or cannula) 40, distal body element 310, compressible tube 315, proximal body element 320, and cap 355 (including passing through septum 357 of cap 355), the assembly is passed through the skin of the patient and secured in a lumen 22 of an access device 10. Then the obturator's snap lock 360 is released, by depressing finger seat 365 so as to release catch 370, and the obturator 106 is removed. At this point, cap 355 (with septum 357) will prevent blood (from the vascular system of the patient) from exiting the proximal end of the assembly. Next, snap lock 340 is activated, by depressing finger seat 345 so as to drive ram 350 into compressible tube 315 and thereby close off the central lumen of compressible tube 315. With the central lumen of compressible tube 315 so closed off, cap 355 may be safely removed from the proximal end of proximal body element 320. Then a blood line (not shown) leading to a dialysis machine (also not shown) is connected to the proximal end of proximal body element 320. Then snap lock 340 is released, thereby permitting blood to flow between the vascular system of the patient and the dialysis machine.

Next, a mirror-image needle (or cannula) and obturator assembly is passed through the skin of the patient, adjacent to the first-passed assembly described above. This second assembly is connected up to the vascular system of the patient and the dialysis machine in the foregoing manner.

Once the two needle (or cannula) and obturator assemblies have been secured to the access device 10, the two assemblies (which are disposed adjacent to one another) may be fastened together. This may be done using their mirror-image flanges 325, 325', in the manner described above.

Alternatively, if desired, the two needle (or cannula) and obturator assemblies may be fastened together, using their mirror-image flanges 325, 325', before the two assemblies are inserted into access device 10.

Or, if desired, the two needle (or cannula) and obturator assemblies may be fastened together at some other point, using some other sequence. For example, a first assembly could be inserted into a lumen 22 of access device 10 and then, before withdrawing its associated obturator 106, a second assembly could be inserted into an adjacent lumen 22' of access device 10 and then, before withdrawing its own associated obturator 106, the two assemblies could be fastened together using their mirror-image flanges 325, 325'. Then the two obturators 106 could be withdrawn, and the two needle (or cannula) and obturator assemblies connected up to a dialysis machine in the manner previously described.

Still other sequences for installing a pair of needle (or cannula) and obturator assemblies of the sort shown in FIGS. 18–23 will be apparent to a person skilled in the art in view of the foregoing disclosure.

At the conclusion of the dialysis session, the assemblies may be quickly and easily dismounted from one another by simple rotational movement, which movement simultaneously releases the two flanges 325, 325' from one another, as well as releases needles (or cannulas) 40 from locking blades 32.

With respect to the needle (or cannula) and obturator assembly shown in FIG. 18, it should also be appreciated that the assembly might be used without connecting it to a mirror-image assembly. Indeed, in such a case, one might provide the needle (or cannula) and obturator assembly shown in FIG. 18, but omit the aforementioned flange 325.

Further Variations

It should also be appreciated that structure other than flanges 325, 325' might be used to connect together two needle (or cannula) and obturator assemblies of the sort shown in FIGS. 18–23. By way of example, the distal body portion 300 might be modified so as to provide connecting structure similar to that shown in FIGS. 10–12, or connecting structure similar to that shown in FIGS. 13–15, or connecting structure similar to that shown in FIG. 16, or connecting structure similar to that shown in FIG. 17. Furthermore, distal body portion 300 might be modified so as to permanently connect together two of the structures, in a manner similar to that shown in FIG. 9.

Similarly, structures analogous to flanges 325, 325' might be used to connect together the two needle (or cannula) and obturator assemblies shown in FIG. 10, 13 or 17.

It will now be apparent to those skilled in the art that still other embodiments, improvements, details, and uses can be made, consistent with the letter and spirit of the foregoing disclosure and within the scope of this patent, which is limited only by the following claims, construed in accordance with the patent law, including the doctrine of equivalents.

What is claimed is:

1. A method for accessing the vascular system of a patient, said method comprising the steps of:

(1) providing a needle and obturator assembly comprising:

a needle having a distal end and a proximal end, said needle comprising a first lumen;

a distal body element having a distal end and a proximal end, said distal end of said distal body element being mounted to said proximal end of said needle, and said distal body element comprising a second lumen, with said second lumen being in communication with said first lumen;

a compressible tube having a distal end and a proximal end, said distal end of said compressible tube being mounted to said proximal end of said distal body element, and said compressible tube comprising a third lumen, with said third lumen being in communication with said second lumen;

a proximal body element having a distal end and a proximal end, said distal end of said proximal body element being mounted to said proximal end of said compressible tube, and said proximal body element comprising a fourth lumen, with said fourth lumen being in communication with said third lumen;

closure means connected to said compressible tube for selectively closing off said third lumen;

a cap having a distal end and a proximal end, said distal end of said cap being removably mounted to said proximal end of said proximal body element, and said cap comprising a fifth lumen, said fifth lumen being in communication with said fourth lumen when said cap is mounted to said proximal body element, and said cap comprising a septum extending transversely across said fifth lumen;

an obturator having a distal end and a proximal end, said obturator being removably disposed in said first lumen, said second lumen, said third lumen, said fourth lumen and said fifth lumen, with said obturator passing through said septum when said obturator is disposed in said fifth lumen; and locking means connected to said proximal end of said obturator for selectively locking said obturator to said cap;

(2) passing said needle assembly through the skin of a patient so that said distal end of said needle is in communication with the vascular system of the patient;

(3) unlocking said locking means;

(4) removing said obturator from said first lumen, said second lumen, said third lumen, said fourth lumen and said fifth lumen;

(5) engaging said closure means so as to close off said third lumen;

(6) removing said cap from said proximal body element; and (7) disengaging said closure means so as to open up said third lumen;

whereby access to the vascular system of the patient will be provided through said first, second, third and fourth lumens.

2. A method according to claim 1 wherein said needle and obturator assembly further comprises attachment means for connecting said distal body element to a like distal body element of a like needle and obturator assembly, and further wherein said method further comprises the step of attaching said needle and obturator assembly to a like needle and obturator assembly, using said attachment means.

3. A method according to claim 2 wherein said step of attaching said needle and obturator assembly to a like needle and obturator assembly takes place after step 7.

4. A method according to claim 2 wherein said step of attaching said needle and obturator assembly to a like needle and obturator assembly takes place after step 1 and before step 2.

5. A method according to claim 2 wherein said step of attaching said needle and obturator assembly to a like needle and obturator assembly takes place after step 4.

6. A method according to claim 1 wherein said method further comprises, after step 6 and before step 7, connecting said proximal end of said proximal body element to a dialysis machine so that said fourth lumen is in communication with the dialysis machine.

7. A needle assembly comprising:

a needle having a distal end and a proximal end, said needle comprising a first lumen;

a distal body element having a distal end and a proximal end, said distal end of said distal body element being mounted to said proximal end of said needle, and said distal body element comprising a second lumen, with said second lumen being in communication with said first lumen;

a compressible tube having a distal end and a proximal end, said distal end of said compressible tube being mounted to said proximal end of said distal body element, and said compressible tube comprising a third lumen, with said third lumen being in communication with said second lumen;

a proximal body element having a distal end and a proximal end, said distal end of said proximal body element being mounted to said proximal end of said compressible tube, and said proximal body element comprising a fourth lumen, with said fourth lumen being in communication with said third lumen;

closure means connected to said compressible tube for selectively closing off said third lumen; and a cap having a distal end and a proximal end, said distal end of said cap being removably mounted to said proximal end of said proximal body element, and said cap comprising a fifth lumen, said fifth lumen being in communication with said fourth when said cap is mounted to said proximal body element, and said cap comprising a septum extending transversely across said fifth lumen;

an obturator having a distal end and a proximal end, said obturator being removably disposed in said first lumen, said second lumen, said third lumen, said fourth lumen and said fifth lumen, with said obturator passing through said septum when said obturator is disposed in said fifth lumen; and locking means connected to said proximal end of said obturator for selectively locking said obturator to said cap.

8. A needle assembly comprising:

a needle having a distal end and a proximal end, said needle comprising a first lumen;

a distal body element having a distal end and a proximal end, said distal end of said distal body element being mounted to said proximal end of said needle, and said distal body element comprising a second lumen, with said second lumen being in communication with said first lumen;

a compressible tube having a distal end and a proximal end, said distal end of said compressible tube being mounted to said proximal end of said distal body element, and said compressible tube comprising a third lumen, with said third lumen being in communication with said second lumen;

a proximal body element having a distal end and a proximal end, said distal end of said proximal body element being mounted to said proximal end of said compressible tube, and said proximal body element comprising a fourth lumen, with said fourth lumen being in communication with said third lumen;

closure means connected to said compressible tube for selectively closing off said third lumen; and a cap having a distal end and a proximal end, said distal end of said cap being removably mounted to said proximal end of said proximal body element, and said cap comprising a fifth lumen, said fifth lumen being in communication with said fourth when said cap is mounted to said proximal body element, and said cap comprising a septum extending transversely across said fifth lumen;

wherein said distal body element comprises attachment means for connecting said distal body element to a like distal body element of a like needle assembly.

9. A needle assembly comprising:

a needle having a distal end and a proximal end, said needle comprising a first lumen;

a distal body element having a distal end and a proximal end, said distal end of said distal body element being mounted to said proximal end of said needle, and said distal body element comprising a second lumen, with said second lumen being in communication with said first lumen;

a compressible tube having a distal end and a proximal end, said distal end of said compressible tube being mounted to said proximal end of said distal body element, and said compressible tube comprising a third lumen, with said third lumen being in communication with said second lumen;

a proximal body element having a distal end and a proximal end, said distal end of said proximal body element being mounted to said proximal end of said compressible tube, and said proximal body element comprising a fourth lumen, with said fourth lumen being in communication with said third lumen;

closure means connected to said compressible tube for selectively closing off said third lumen; and a cap having a distal end and a proximal end, said distal end of said cap being removably mounted to said proximal end of said proximal body element, and said cap comprising a fifth lumen, said fifth lumen being in communication with said fourth when said cap is mounted to said proximal body element, and said cap comprising a septum extending transversely across said fifth lumen;

wherein said distal body element comprises attachment means for connecting said distal body element to a like distal body element of a like needle assembly; and wherein said attachment means comprise a flange extending outboard of said distal body element, and further wherein said flange comprises a protuberance extending out of said flange and a recess extending into said flange.

* * * * *